United States Patent
Lykke-Hartmann et al.

(10) Patent No.: US 11,666,561 B2
(45) Date of Patent: Jun. 6, 2023

(54) COMPOUNDS FOR USE IN REGULATING FOLLICLE MATURATION

(71) Applicant: AARHUS UNIVERSITET, Aarhus C (DK)

(72) Inventors: Karin Lykke-Hartmann, Skodstrup (DK); Emil Hagen Ernst, Silkeborg (DK); Anders Heuck, Skanderborg (DK)

(73) Assignee: AARHUS UNIVERSITET, Aarhus C (DK)

( * ) Notice: Subject to any disclaimer, the term of this patent is extended or adjusted under 35 U.S.C. 154(b) by 628 days.

(21) Appl. No.: 16/616,769

(22) PCT Filed: May 31, 2018

(86) PCT No.: PCT/EP2018/064359
§ 371 (c)(1),
(2) Date: Nov. 25, 2019

(87) PCT Pub. No.: WO2018/220126
PCT Pub. Date: Dec. 6, 2018

(65) Prior Publication Data
US 2021/0145809 A1  May 20, 2021

(30) Foreign Application Priority Data

Jun. 1, 2017  (EP) .................... 17173965

(51) Int. Cl.
| *A61K 36/00* | (2006.01) |
| *A61K 31/4425* | (2006.01) |
| *A61P 15/08* | (2006.01) |
| *A61K 9/00* | (2006.01) |
| *A61K 35/54* | (2015.01) |
| *C12N 5/073* | (2010.01) |

(52) U.S. Cl.
CPC ........ *A61K 31/4425* (2013.01); *A61K 9/0034* (2013.01); *A61K 35/54* (2013.01); *A61P 15/08* (2018.01); *C12N 5/0604* (2013.01)

(58) Field of Classification Search
None
See application file for complete search history.

(56) References Cited

U.S. PATENT DOCUMENTS

| 2008/0221173 A1* | 9/2008 | Bhaskaran | A61K 31/198 514/356 |
| 2011/0142974 A1* | 6/2011 | Friedel | A23L 33/15 514/356 |
| 2014/0154346 A1* | 6/2014 | Bhaskaran | A61P 43/00 424/725 |

OTHER PUBLICATIONS

Aswar et al. (2009) Inter. J. Green Pharmacy Jul.-Sep. 220-223. (Year: 2009).*
Rao et al. (2015) Phytother. Res. 29: 1123-1130. (Year: 2015).*
Sureshkumar et al. (2018) Toxicology Rep. 5: 1060-1068. (Year: 2018).*
Begum et al. (2016) Phytother. Res. 30: 1775-1784. (Year: 2016).*
Khanna et al. (2021) Clinical Phytoscience 7: 63 (12 pages). (Year: 2021).*
Mohamadi et al. (2018) J. Dietary Supplements vol. 15, No. 2, 207-222. (Year: 2018).*
Venkata et al. (2017) Mol. Nutr. Food Res. 61, 6, 1600530 (26 pages) (Year: 2017).*
Adhikari et al; Human Molecular Genetics, vol. 21, No. 11, pp. 2476-2484. Year: 2012.
Adhikari et al; Molecular Human Reproduction, vol. 15, No. 12, pp. 765-770. Year: 2009.
Andersen et al; Human Reproduction vol. 23, No. 10, pp. 2266-2272. Year: 2008.
Bonnet et al; BMC Genomics; 14:904, pp. 1-19. Year: 2013.
Hu et al; PLoS One; 12(1):e0170409; doi: 10.1371/journal.pone.0170409. Year: 2017.
Kai et al; Reproductive Biology and Endocrinology; 13:27. Year: 2015.
Kristensen et al; Molecular and Cellular Endocrinology 401; pp. 189-201. Year: 2015.
Lu X et al; Reproduction; 153(5):683-694; doi: 10.1530/REP-16-0577 (Abstract only). Year: 2017.
Markholt et al; Molecular Human Reproduction, vol. 18, No. 2, pp. 96-110. Year: 2012.
Novella-Maestre et al; PLOS ONE; DOI:10.1371/journal.pone.0127786. Year: 2015.
Rosendahl et al; Reproductive BioMedicine Online; vol. 22, pp. 162-171. Year: 2011.
Schmidt et al; Human Reproduction; vol. 19, No. 12, pp. 2806-2810. Year: 2004.
Begum et al; Phytotherapy Research, vol. 30, No. 11, pp. 1775-1784. Year: 2016.
Lee, Tsung-Ming et al; Free Radical Biology and Medicine, vol. 77. Year: 2014.
Ma, Rujun et al; PLOS ONE; vol. 12, No. 5, e0177844. Year: 2017.
Mohan, V. et al; International Journal of Green Pharmacy, vol. 3, No. 3, pp. 220-223. Year: 2009.
Rao, Faiza et al; International Journal of Molecular Sciences; vol. 17, No. 8; p. 1269. Year: 2016.
Zhai, Jun et al; J Clin Endocrinol Metab.; 101(11); pp. 4405-4412. Year: 2016.

* cited by examiner

*Primary Examiner* — Russell G Fiebig
(74) *Attorney, Agent, or Firm* — Dinsmore & Shohl LLP

(57) ABSTRACT

A compound and methods are provided for treating, preventing or ameliorating infertility or reduced fertility in an individual, wherein said compound is capable of regulating the activity of Nuclear Factor, Erythroid 2 Like 2 (NFE2L2).

10 Claims, 10 Drawing Sheets
Specification includes a Sequence Listing.

COMPOUNDS FOR USE IN REGULATING FOLLICLE MATURATION

TECHNICAL FIELD

The present invention relates to a method for screening for a compound that regulates follicle maturation, compounds that regulates follicle maturation, for use in treating, preventing or ameliorating an ovulation disorder and methods for treating females having an ovulation disorder.

BACKGROUND

Activation of primordial follicles is marked morphologically by the primordial-to-primary transition when the flattened granulosa cells start proliferation and become cuboidal and the oocyte grows in size. The primordial-to-primary follicle transition is a gradual process in which intermediate follicles with both flattened and cuboidal granulosa cells can be noted. Maintaining dormancy of primordial follicles on one hand, and gradual activation towards ovulation on the other, is a tightly regulated process involving several pathways (Bonnet et al., 2013). Activators and inhibitors of the primordial-to-primary follicle transition are known to be important for its regulation. For example, conditional ablation of Foxo3a, Pten, and Tsc1/2 in oocytes triggers increased oocyte activation (Adhikari et al., 2009, Adhikari et al., 2012). Also, in vitro culture of human ovarian tissue with PTEN inhibition, and AKT stimulation has been shown to increase primordial follicle activation (Novella-Maestre et al., 2015). Studies on human oocytes have been performed on a pool of isolated oocytes from primordial, intermediate and primary follicles (Markholt et al., 2012) or in combination with the surrounding granulosa cells (Kristensen et al., 2015). However, it has not been possible to specifically dissect gene expression in oocytes from primordial and primary follicles, respectively.

Ovarian deficits and consequently infertility are a growing problem worldwide and is often attributed to compromised or poor egg production in females. Treatment for infertility is a major challenge with numerous negative socio-economic and patient psychological implications. Pushing forward egg maturation may help women with for example age related decline in eggs and/or women with pathologies such as for example Polycystic Ovary Syndrome. One major challenge is to protect the pool of resting eggs, i.e. the reproductive potential, from premature expiration. Thus, holding back egg maturation may help women who need to maintain an egg pool, for example during disease treatment, such as cancer treatment, or due to genetic diseases or disorders causing premature depletion of eggs. Therefore, there is a great need to control the most important early steps of egg development.

SUMMARY

The inventors of the present invention have identified compounds for use in regulating follicle maturation, in particular for use in regulating the primordial to primary transition of follicles. Transcriptome dynamics specifically associated with human oocytes from primordial and primary follicles, respectively, have been characterized and used to identify targets and screen for potential compounds that can regulate follicle maturation, in particular early stages of follicle maturation such as the primordial to primary transition.

Accordingly, one aspect of the present invention relates to a method for screening for a compound that regulates follicle maturation, wherein said method comprises
a. selecting a compound known to regulate the activity of at least one of the candidates identified in table 1 and/or 2.
b. contacting primordial and/or primary ovaries with said compound determining whether said compound is capable of regulating follicle maturation by determining the amount of primordial follicles and/or primary follicles and compare it with a control.

The method has been used to identify compounds described below.

Thus, one aspect of the present invention relates to a compound for use in regulating follicle maturation, wherein said compound can regulate the activity of 6-phosphfructo-2-kinase.

In a preferred embodiment said compound is an inhibitor of 6-phosphfructo-2-kinase. Preferably, said compound promotes follicle maturation. In a specific embodiment said compound is 3-(3-pyridinyl)-1-(4-pyridinyl)-2-propen-1-one (3PO).

In a specific aspect, a compound is provided for use in treating, preventing or ameliorating infertility or reduced fertility in an individual, wherein said compound is capable of regulating the activity of Nuclear Factor, Erythroid 2 Like 2 (NFE2L2).

A method is also provided for treating, preventing or ameliorating infertility or reduced fertility in an individual, said method comprising administering to said individual a therapeutically effective amount of a compound is capable of regulating the activity of Nuclear Factor, Erythroid 2 Like 2 (NFE2L2).

The compound is preferably an inhibitor of NFE2L2.

In another aspect, a method is provided for stimulating follicle maturation, said method comprising
a) providing a source of primordial follicles,
b) providing a compound capable of regulating the activity of Nuclear Factor, Erythroid 2 Like 2 (NFE2L2), and
c) bringing said compound into contact with said source of primordial follicles.

The method may merely comprise is a sample of primordial follicles,
a) providing a compound capable of regulating the activity of Nuclear Factor, Erythroid 2 Like 2 (NFE2L2), and
b) bringing said compound into contact with said source of primordial follicles.

This method can be an in vitro method, and the compound is preferably a compound being capable of stimulating primordial to primary transition of follicles.

Another aspect of the present invention relates to a compound for use in regulating follicle maturation, wherein said compound can regulate the activity of protein kinase AMP-activated catalytic subunit alpha 1 (PRKAA1).

In a preferred embodiment said compound is an activator of PRKAA1. Preferably, said compound inhibits follicle maturation. In a specific embodiment said compound is 5-aminoimidazole-4-carboxamide-1β-D-ribofuranoside (AICAR).

Another aspect of the present invention relates to a compound for use in regulating follicle maturation, wherein said compound can regulate the activity of Platelet-derived growth factor receptor α (PDGFRA)

In a preferred embodiment said compound is an activator of PDGFRA. Preferably, said compound promotes follicle maturation. In a specific embodiment said compound comprises an amino acid sequence having at least 80% sequence identity with SEQ ID NO: 1.

Another aspect of the present invention relates to a compound for use in regulating follicle maturation, wherein said compound can regulate the activity of Phosphodiesterase 8B (PDE8B).

In a preferred embodiment said compound is an inhibitor of PDE8B. Preferably, said compound inhibits follicle maturation. In a specific embodiment said compound is 4,9-dihydro-4-(1-methyl-4-piper-idylidende)-10H-benzo(4,5)cyclohepta(1,2,b)thiophen-10-one (Ketotifen).

Another aspect of the present invention relates to a compound for use in regulating follicle maturation, wherein said compound can regulate the activity of Phosphodiesterase 3B (PDE3B).

In a preferred embodiment said compound is an inhibitor of PDE3B. Preferably, said compound inhibits follicle maturation. In a specific embodiment said compound is selected from the group consisting of 7-(2,3-dihydroxypropyl)-1,3-dimethylpurine-2,6-dione (dyphylline), 5-methyl-1H-1,6-naphthyridin-2-one (medorinone), 6-[4-(1-cyclohexyltetrazol-5-yl)butoxy]-3,4-dihydro-1H-quinolin-2-one (cilostazol), 2-[[2-[bis(2-hydroxyethyl)amino]-4,8-di(piperidin-1-yl)pyrimido[5,4-d]pyrimidin-6-yl]-(2-hydroxyethyl)amino]ethanol (dipyridamole), 3-amino-5-pyridin-4-yl-1H-pyridin-2-one (amrinone), 1-butyl-3-(4-methylphenyl)sulfonylurea (tolbutamide), 1,3-dimethyl-7H-purine-2,6-dione (theophylline) and 3,7-dimethyl-1-(5-oxohexyl)purine-2,6-dione (pentoxifylline).

Another aspect of the present invention relates to a compound for use in regulating follicle maturation, wherein said compound can regulate the activity of Carbamoyl-Phosphate Synthase 1 (CPS1).

In a preferred embodiment said compound is an inhibitor of CPS1. Preferably, said compound inhibits follicle maturation. In a specific embodiment said compound is ((2S)-2-(carbamoylamino)pentanedioic acid (N-Carbamyl-L-glutamic acid).

Another aspect of the present invention relates to a compound for use in regulating follicle maturation, wherein said compound can regulate the activity of Nuclear Factor, Erythroid 2 Like 2 (NFE2L2).

In a preferred embodiment said compound is an inhibitor of NFE2L2. Preferably, said compound promotes follicle maturation. In a specific embodiment said compound is 1-methylpyridin-1-ium-3-carboxylic acid; chloride (Trigonellin hydrochloride).

Another aspect of the present invention relates to a compound for use in regulating follicle maturation, wherein said compound can regulate the activity of Protein Tyrosine Kinase 2 Beta (PTK2B).

In a preferred embodiment said compound is an inhibitor of PTK2B. Preferably, said compound inhibits follicle maturation. In a specific embodiment said compound is selected from the group consisting of N-methyl-N-[3-[[[2-[(2-oxo-1,3-dihydroindol-5-yl)amino]-5-(trifluoromethyl)pyrimidin-4-yl]amino]methyl]pyridin-2-yl]methanesulfonamide (PF-562271) and CT-707.

Another aspect of the present invention relates to a compound for use in regulating follicle maturation, wherein said compound can regulate the activity of MDM2.

In a preferred embodiment said compound is an inhibitor of MDM2. Preferably, said compound promotes follicle maturation. In a specific embodiment said compound is selected from the group consisting of 1-N-[2-(1H-indol-3-yl)ethyl]-4-N-pyridin-4-ylbenzene-1,4-diamine (serdemetan), (1S)-1-(4-chlorophenyl)-6-methoxy-2-[4-[methyl-[[4-(4-methyl-3-oxopiperazin-1-yl)cyclohexyl]methyl]amino]phenyl]-7-propan-2-yloxy-1,4-dihydroisoquinolin-3-one (CGM097), L-Erythro-hexonamide, 2,6-anhydro-5-((((3'R,4'S,5'R)-6"-chloro-4'-(2-chloro-3-fluoro-4-pyridinyl)-1",2"-dihydro-4,4-dimethyl-2"-oxodispiro(cyclohexane-1,2'-pyrrolidine-3',3"-(3H)indol)-5'-yl)carbonyl)amino)-3,4,5-trideoxy-, 4-methylbenzenesulfon (DS-3032b), 4-amino-1-[(2R,3S,4S,5R)-3,4-dihydroxy-5-(hydroxymethyl)oxolan-2-yl]pyrimidin-2-one (MK-8242), (6S)-5-(5-chloro-1,2-dihydro-1-methyl-2-oxo-3-pyridinyl)-6-(4-chlorophenyl)-2-(2,4-dimethoxy-5-pyrimidinyl)-5,6-dihydro-1-(1-methylethyl)-Pyrrolo[3,4-d]imidazol-4(1H)-one (HDM201), ALRN-6924, 4-{[(3S,4R,5S)-3-(3-Chloro-2-fluorophenyl)-4-(4-chloro-2-fluorophenyl)-4-cyano-5-(2,2-dimethylpropyl)-D-prolyl]amino}-3-methoxybenzoic acid (idasanutlin), RO6839921, [(4S,5R)-2-(4-tert-butyl-2-ethoxyphenyl)-4,5-bis(4-chlorophenyl)-4,5-dimethylimidazol-1-yl]-[4-(3-methylsulfonylpropyl)piperazin-1-yl]methanone (RO-5045337), 2-[(3R,5R,6S)-5-(3-chlorophenyl)-6-(4-chlorophenyl)-3-methyl-1-[(2S)-3-methyl-1-propan-2-ylsulfonylbutan-2-yl]-2-oxopiperidin-3-yl]acetic acid (AMG-232) and APG-115.

Another aspect of the present invention relates to a compound for use in regulating follicle maturation, wherein said compound can regulate the activity of Erb-B2 Receptor Tyrosine Kinase 4 (ERBB4).

In a preferred embodiment said compound is an inhibitor of Erb-B2 Receptor Tyrosine Kinase 4 (ERBB4). Preferably, said compound inhibits follicle maturation. In a specific embodiment said compound is selected from the group consisting of [(3S)-morpholin-3-yl]methyl N-[4-[[1-[(3-fluorophenyl)methyl]indazol-5-yl]amino]-5-methylpyrrolo[2,1-f][1,2,4]triazin-6-yl]carbamate (BMS-599626), (E)-N-[4-(3-chloro-4-fluoroanilino)-7-[(3S)-oxolan-3-yl]oxyquinazolin-6-yl]-4-(dimethylamino)but-2-enamide (afatinib), N-[2-[2-(dimethylamino)ethyl-methylamino]-4-methoxy-5-[[4-(1-methylindol-3-yl)pyrimidin-2-yl]amino]phenyl]prop-2-enamide (osimertinib), 1-[4-[4-(3,4-dichloro-2-fluoroanilino)-7-methoxyquinazolin-6-yl]oxypiperidin-1-yl]prop-2-en-1-one (poziotinib), 4-methyl-N-[3-(4-methylimidazol-1-yl)-5-(trifluoromethyl)phenyl]-3-[(4-pyridin-3-ylpyrimidin-2-yl)amino]benzamide (pirotinib) and (E)-N-[4-(3-chloro-4-fluoroanilino)-3-cyano-7-ethoxyquinolin-6-yl]-4-(dimethylamino)but-2-enamide (pelitinib).

Another aspect of the present invention relates to a compound for use in regulating follicle maturation, wherein said compound can regulate the activity of Dual Specificity Protein Kinase (TKK).

In a preferred embodiment said compound is an inhibitor of TKK. Preferably, said compound inhibits follicle maturation. In a specific embodiment said compound is methyl 2,6-dimethyl-5-nitro-4-[2-(trifluoromethyl)phenyl]-1,4-dihydropyridine-3-carboxylate (BAY 1217389).

Another aspect of the present invention relates to a compound for use in regulating follicle maturation, wherein said compound can regulate the activity of B Lymphoid Tyrosine Kinase (BLK).

In a preferred embodiment said compound is an inhibitor of BLK. Preferably, said compound inhibits follicle maturation. In a specific embodiment said compound is N-[2-[2-(dimethylamino)ethyl-methylamino]-4-methoxy-5-[[4-(1-methylindol-3-yl)pyrimidin-2-yl]amino]phenyl]prop-2-enamide (osimertinib).

Another aspect of the present invention relates to a compound for use in regulating follicle maturation, wherein said compound can regulate the activity of Insulin Like Growth Factor 1 Receptor (IGF1R).

In a preferred embodiment said compound is an inhibitor of IGF1R. Preferably, said compound inhibits follicle maturation. In a specific embodiment said compound is selected from the group consisting of (5R,5aR,8aS,9R)-5-hydroxy-9-(3,4,5-trimethoxyphenyl)-5a,6,8a,9-tetrahydro-5H-[2]benzofuro[5,6-f][1,3]benzodioxol-8-one (picropodophyllin), 3-[8-amino-1-(2-phenylquinolin-7-yl)imidazo[1,5-a]pyrazin-3-yl]-1-methylcyclobutan-1-ol)(LC Laboratories (linsitinib), cixutumumab, N-(2-chloro-6-methylphenyl)-2-[[6-[4-(2-hydroxyethyl)piperazin-1-yl]-2-methylpyrimidin-4-yl]amino]-1,3-thiazole-5-carboxamide (ganitumab), ((E)-N-[4-[3-chloro-4-(pyridin-2-ylmethoxy)anilino]-3-cyano-7-ethoxyquinolin-6-yl]-4-(dimethylamino)but-2-enamide (Neratinib), 4-N-(5-cyclopropyl-1H-pyrazol-3-yl)-6-(4-methylpiperazin-1-yl)-2-N-[(3-propan-2-yl-1,2-oxazol-5-yl)methyl]pyrimidine-2,4-diamine (XL228), 4-[4-[[4-chloro-3-(trifluoromethyl)phenyl]carbamoylamino]phenoxy]-N-methyl-pyridine-2-carboxamide (BIIB022), 4-amino-N-(1-azabicyclo[3.3.1]nonan-4-yl)-5-chloro-2-methoxybenzamide) (dalotuzumab) and MM-141.

Another aspect of the present invention relates to a compound for use in regulating follicle maturation, wherein said compound can regulate the activity of Insulin Like Growth Factor 2 (IGF2).

In a preferred embodiment said compound is an inhibitor of IGF2. Preferably, said compound inhibits follicle maturation. In a specific embodiment said compound is BI 836845.

In one embodiment, the compounds as described herein and above are for use in regulating follicle maturation in vitro.

In another embodiment, the compounds as described herein for use in regulating follicle maturation in vivo.

In a preferred embodiment of the present invention, the compounds are for use in regulating primordial to primary transition of follicles. Preferably, said follicles are mammalian follicles. It is preferred that said mammalian is a human.

A further aspect of the present invention relates to a compound as defined herein for use in treating, preventing or ameliorating an ovulation disorder.

In one embodiment said ovulation disorder is selected from the group consisting of Polycystic ovary syndrome (PCOS), Premature ovarian failure (P01), Hypothalamic dysfunction and Menopause.

In another embodiment said ovulation disorder is caused by hyperprolactinemia.

Yet another aspect of the present invention relates to a pharmaceutical composition comprising at least one compound as defined herein for use in treating, preventing or ameliorating infertility or reduced fertility in a female individual.

Preferably, said pharmaceutical composition further comprises at least one pharmaceutically acceptable carrier. In another embodiment said pharmaceutical composition further comprises an additional active agent.

Said pharmaceutical composition may for example be administered in vitro to primordial follicles from said individual.

In one preferred embodiment said female individual is a female mammal. Preferably, said female mammal is a female human.

Another aspect of the present invention relates to a method for treating, preventing or ameliorating infertility of a female individual having an ovulation disorder, comprising administering to said individual a therapeutically effective amount of a compound as defined herein.

Preferably, said female individual is a female mammal, such as a female human.

In a specific embodiment of the compound for use or methods provided herein, the treatment comprises the steps of a. removing ovulated oocytes from said individual,
b. subjected said said ovulated oocyte to in vitro fertilization thereby obtaining a fertilized oocyte leading to a zygote,
c. culturing said zygote in order to obtain a multicellular blastocyst, and
d. transferring said blastocystinto the uterus of a said individual and/or a surrogate mother.

A is also provided for stimulating follicle maturation, said method comprising
a) providing a compound capable of regulating the activity of Nuclear Factor, Erythroid 2 Like 2 (NFE2L2), and
b) bringing said compound into contact with said source of primordial follicles.

DETAILED DESCRIPTION

Definitions

Figure 1:
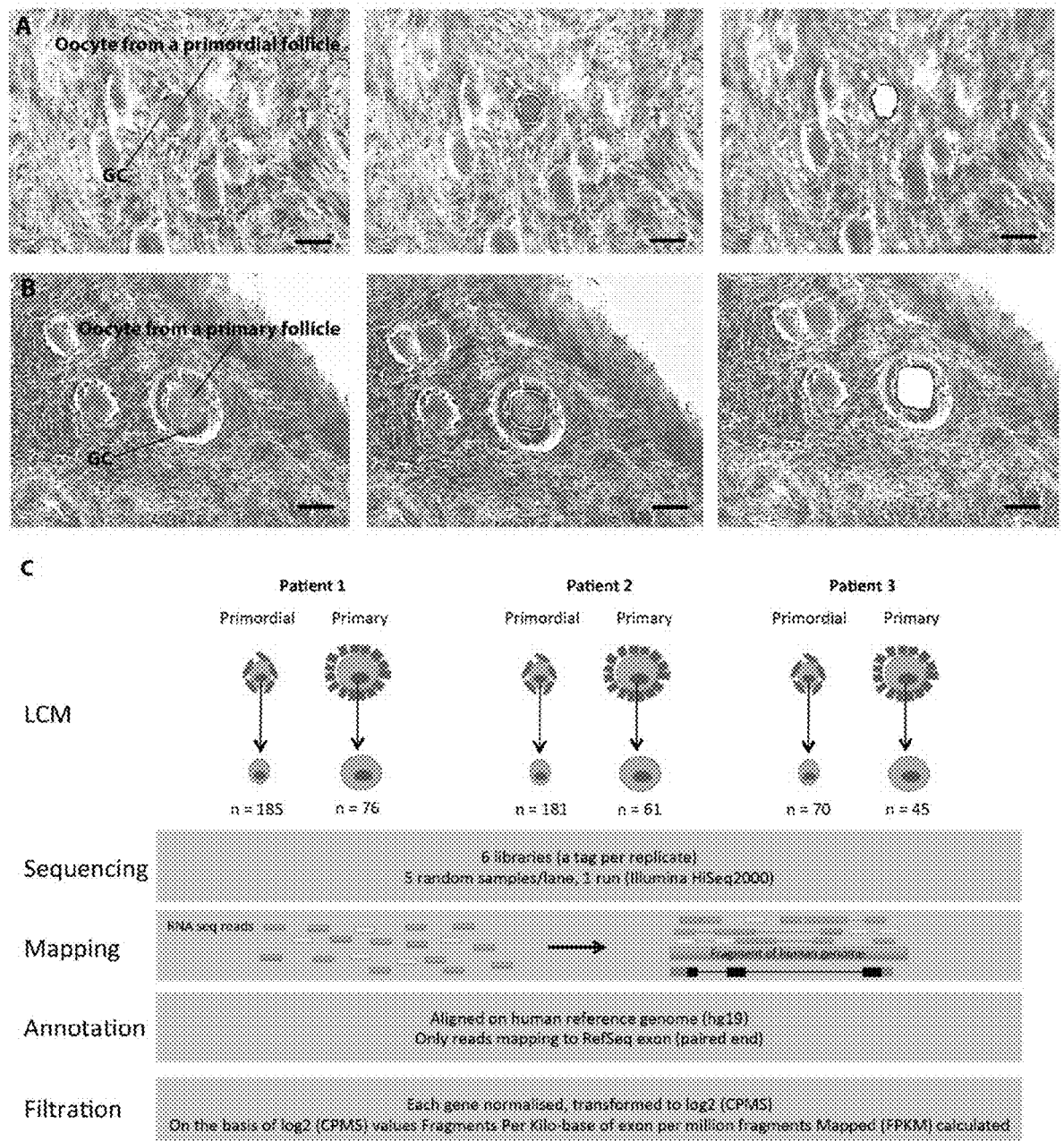
FIG. 1: Experimental design for Laser Capture Microdissection and sequencing (A-B) Identification, laser cutting and after capture of oocytes from primordial (A) and primary (B) follicles, revealing the precision in which stage-specific oocytes were isolated. Oocytes from primordial and primary follicles, as well as granulosa cells (GC) is indicated by bars. Scale bar 50 μm. (C) Oocytes from primordial (N=3 patients; n=185, n=181, n=70 oocytes) and primary (N=3 patients; n=76, n=61=n=45 oocytes) follicles were isolated from three different patients (patient 1-3). Subsequently, the cap-adhered oocyte was lysed for mRNA isolation, cDNA synthesis, and RNA sequencing. After sequencing, mapping of the data to the human genome was performed before annotation. Finally, each gene was normalised by transforming to the log 2(CPMS).

The term "ovary" as used herein refers to the ovum-producing reproductive organ, which is the site of production and periodical release of egg cells, the female gametes. In the ovaries, the developing egg cell (or oocyte) grows within the environment provided by follicles.

The term "follicle" as used herein refers to a roughly spheroid cellular aggregation set found in the ovaries. The follicle is an anatomical structure in which the primary oocyte develops. Follicles are composed of different types and number of cells according to the stage of their maturation, and their size is indicative of the stage of oocyte development.

The term "primordial follicle" as used herein refers to the follicles that are formed in the female ovary at 18-22 weeks post-conception. The primordial follicles contain immature oocytes surrounded by flat, squamous granulosa cells (the support cells) that are segregated from the oocyte's environment by the basal lamina. They are quiescent, showing little to no biological activity.

The term "primary follicle" as used herein refers to the follicle that are formed when the granulosa cells of these primordial follicles change from a flat to a cuboidal structure, marking the beginning of the primary follicle. Both the oocyte and the follicle grow dramatically, increasing to almost 0.1 mm in diameter. A glycoprotein polymer capsule called the zona pellucida forms around the oocyte, separating it from the surrounding granulosa cells.

The term "primordial oocyte" as used herein refers to an oocyte from a primordial follicle.

The term "primary oocyte" as used herein refers to an oocyte from a primary follicle.

The term "primordial to primary transition of follicles" as used herein refers to the stage at which the follicle develops from a primordial follicle into a primary follicle. Thus, the primordial to primary transition is the process by which primordial follicle 'wakes up' and matures or develops into a primary follicle. For example, when a compound promotes the primordial to primary transition of follicles, it is meant that the compound promotes or activates the maturation of primordial follicles into primary follicles. When a compound inhibits the primordial to primary transition of follicles, it is meant that the compound inhibits the maturation of primordial follicles into primary follicles or simply keeps the primordial follicles in the dormant stage.

Method for Screening for Compounds

One aspect of the present invention relates to a method for screening for a compound that regulates follicle maturation, wherein said method comprises
  c. selecting a compound known to regulate the activity of at least one of the candidates identified in table 1 and/or 2.

d. contacting a primordial and/or a primary ovary with said compound
e. determining whether said compound is capable of regulating follicle maturation by determining the amount of primordial follicles and/or primary follicles and compare it with a control.

Methods for determining whether said compound is capable of regulating follicle development are described in the example section.

In one embodiment the compound to be tested is dissolved in suitable solvent and added to a culture medium comprising primordial and/or primary ovaries. As a control, solvent not comprising the compound can be added to the culture medium.

The ovary can be a mammalian ovary such as for example a mouse ovary or a human ovary.

The compound may also be contacted with a biopsy from an ovary, in particular a biopsy from a human ovary.

The concentration of the compound in the culture medium depends on the compound to be tested. In one embodiment, the concentration of compound is at least 0.01 micromolar (μm), such as at least 0.1 μM, at least 0.5 μM, at least 1 μM or at least 5

In one embodiment the concentration of compound is between 0.01 μM and 100 millimolar (mM), such as between 0.01 μM and 50 mM or such as between 0.1 μM and 50 mM.

The incubation time may for example be at least 10 hours, at least 24 hours, at least 48 hours, at least 72 hours or at least 96 hours. In one embodiment the incubation time is 1 day, 2 days, 3 days, 4 days or 5 days.

The primordial and/or primary ovaries are preferably incubated with the compound at 37° C. In particular, the primordial and/or primary ovaries are preferably incubated with the compound at 37° C. and 5% $CO_2$.

The number of primordial and primary follicles can be determined using microscopy to visualize the morphology of the ovaries. Please see experimental section for further details.

Compounds for Use in Regulating Follicle Maturation

Compounds identified by the method described above are discussed below.

6-Phosphfructo-2-Kinase as a Target

One aspect of the present invention relates to a compound for use in regulating follicle maturation, wherein said compound can regulate the activity of 6-phosphfructo-2-kinase (PFKFB3).

PFKFB3 was found to be significantly consistently expressed in primordial oocytes and in primary oocytes. In addition, it was found that regulation of PFKFB3 results in a regulation of follicle maturation. More specifically, inhibition of PFKFB3 promotes follicle maturation.

Thus, in a preferred embodiment, said compound is an inhibitor of 6-phosphfructo-2-kinase. In another preferred embodiment, said compound or said inhibitor promotes follicle maturation. In a preferred embodiment said compound or inhibitor of PFKFB3 regulates the primordial to primary transition of follicles. In a particular preferred embodiment said compound or inhibitor of PFKFB3 promotes the primordial to primary transition of follicles.

In a particular preferred embodiment, said compound or said inhibitor is 3-(3-pyridinyl)-1-(4-pyridinyl)-2-propen-1-one (3PO). 3PO is an inhibitor of PFKFB3.

Thus, a preferred embodiment of the present invention relates to 3PO for use in regulating follicle maturation, such as for use in regulating the primordial to primary transition of follicles. A particular preferred embodiment relates to 3PO for use in promoting follicle maturation, such as for use in promoting the primordial to primary transition of follicles.

Protein Kinase AMP-Activated Catalytic Subunit Alpha as a Target

Another aspect of the present invention relates to a compound for use in regulating follicle maturation, wherein said compound can regulate the activity of protein kinase AMP-activated catalytic subunit alpha 1 (PRKAA1).

PRKAA1 was found to be significantly consistently expressed in primordial oocytes and in primary oocytes. In addition, it was found that regulation of PRKAA1 results in a regulation of follicle maturation. More specifically, activation of PRKAA1 inhibits follicle maturation.

Thus, in a preferred embodiment, said compound is an activator of PRKAA1. In another preferred embodiment, said compound or said activator inhibits follicle maturation. In a preferred embodiment said compound or activator of PRKAA1 regulates the primordial to primary transition of follicles. In a particular preferred embodiment said compound or inhibits of PRKAA1 inhibits the primordial to primary transition of follicles.

In a particular embodiment, said compound or said activator is 5-aminoimidazole-4-carboxamide-1β-D-ribofuranoside (AICAR). AICAR is an activator of PRKAA1.

Thus, a preferred embodiment of the present invention relates to AICAR for use in regulating follicle maturation, such as for use in regulating the primordial to primary transition of follicles. A particular preferred embodiment relates to AICAR for use in inhibiting follicle maturation, such as for use in inhibiting the primordial to primary transition of follicles.

Platelet-Derived Growth Factor Receptor a

A further aspect of the present invention relates to a compound for use in regulating follicle maturation, wherein said compound can regulate the activity of Platelet-derived growth factor receptor a (PDGFRA)

PDGFRA was found to be significantly consistently expressed in primordial oocytes and in primary oocytes.

In one embodiment activation of PDGFRA promotes follicle maturation. Thus, preferably, said compound is an activator of PDGFRA. In another preferred embodiment, said compound or said activator promotes follicle maturation. In a preferred embodiment said compound or activator of PDGFRA regulates the primordial to primary transition of follicles. In a particular preferred embodiment said compound or said activator of PDGFRA promotes the primordial to primary transition of follicles.

In a particular embodiment, said compound comprises an amino acid sequence having at least 75% sequence identity with SEQ ID NO: 1, such as at least 80% sequence identity, such as at least 85% sequence identity, such as at least 90% sequence identity, such as at least 95% sequence identity, such as at least 96% sequence identity, such as at least 97% sequence identity, such as at least 98% sequence identity or such as at least 99% sequence identity with SEQ ID NO: 1.

SEQ ID NO:1 encodes the peptide PDGF-AA that binds and activates PDGFRA

Phosphodiesterase 8B as a Target

Yet another aspect of the present invention relates to a compound for use in regulating follicle maturation, wherein said compound can regulate the activity of Phosphodiesterase 8B (PDE8B).

PDE8B was found to be significantly consistently expressed in primordial oocytes (see and in primary oocytes. In addition, it was found that regulation of PDE8B results in a regulation of follicle maturation. More specifically, inhibition of PDE8B inhibits follicle maturation.

Thus, in a preferred embodiment, said compound is an inhibitor of PDE8B. In another preferred embodiment, said compound or said inhibitor inhibits follicle maturation. In a preferred embodiment said compound or inhibitor of PDE8B regulates the primordial to primary transition of follicles. In a particular preferred embodiment said compound or inhibitor of PDE8B inhibits the primordial to primary transition of follicles.

In a particular embodiment, said compound or said inhibitor is 4,9-dihydro-4-(1-methyl-4-piper-idylidende)-10H-benzo(4,5)cyclohepta(1,2,b)thiophen-10-one. 4,9-dihydro-4-(1-methyl-4-piper-idylidende)-10H-benzo(4,5)cyclohepta (1,2,b)thiophen-10-one is also known as ketotifen. Ketotifen is an inhibitor of PDE8B.

Thus, a preferred embodiment of the present invention relates to ketotifen for use in regulating follicle maturation, such as for use in regulating the primordial to primary transition of follicles. A particular preferred embodiment relates to ketotifen for use in inhibiting follicle maturation, such as for use in inhibiting the primordial to primary transition of follicles.

Phosphodiesterase 3B as a Target

A further aspect of the present invention relates to a compound for use in regulating follicle maturation, wherein said compound can regulate the activity of Phosphodiesterase 3B (PDE3B).

PDE3B was found to be significantly consistently expressed in primordial oocytes (see and in primary oocytes.

In one embodiment inhibition of PDE3B inhibits follicle maturation. Thus, preferably, said compound is an inhibitor of PDE3B. In another preferred embodiment, said compound or said inhibitor inhibits follicle maturation. In a preferred embodiment said compound or inhibitor of PDE3B regulates the primordial to primary transition of follicles. In a particular preferred embodiment said compound or inhibitor of PDE3B inhibits the primordial to primary transition of follicles.

In one embodiment said compound is selected from the group consisting of 7-(2,3-dihydroxypropyl)-1,3-dimethylpurine-2,6-dione (dyphylline), 5-methyl-1H-1,6-naphthyridin-2-one (medorinone), 6-[4-(1-cyclohexyltetrazol-5-yl)butoxy]-3,4-dihydro-1H-quinolin-2-one (cilostazol), 2-[[2-[bis(2-hydroxyethyl)amino]-4,8-di(piperidin-1-yl)pyrimido[5,4-d]pyrimidin-6-yl]-(2-hydroxyethyl)amino]ethanol (dipyridamole), 3-amino-5-pyridin-4-yl-1H-pyridin-2-one (amrinone), 1-butyl-3-(4-methylphenyl)sulfonylurea (tolbutamide), 1,3-dimethyl-7H-purine-2,6-dione (theophylline) and 3,7-dimethyl-1-(5-oxohexyl)purine-2,6-dione (pentoxifylline).

Thus, a preferred embodiment of the present invention relates to a compound selected from the group consisting of 7-(2,3-dihydroxypropyl)-1,3-dimethylpurine-2,6-dione (dyphylline), 5-methyl-1H-1,6-naphthyridin-2-one (medorinone), 6-[4-(1-cyclohexyltetrazol-5-yl)butoxy]-3,4-dihydro-1H-quinolin-2-one (cilostazol), 2-[[2-[bis(2-hydroxyethyl)amino]-4,8-di(piperidin-1-yl)pyrimido[5,4-d]pyrimidin-6-yl]-(2-hydroxyethyl)amino]ethanol (dipyridamole), 3-amino-5-pyridin-4-yl-1H-pyridin-2-one (amrinone), 1-butyl-3-(4-methylphenyl)sulfonylurea (tolbutamide), 1,3-dimethyl-7H-purine-2,6-dione (theophylline) and 3,7-dimethyl-1-(5-oxohexyl)purine-2,6-dione (pentoxifylline) for use in regulating follicle maturation, such as for use in regulating the primordial to primary transition of follicles.

A particular preferred embodiment relates to a compound selected from the group consisting of 7-(2,3-dihydroxypropyl)-1,3-dimethylpurine-2,6-dione (dyphylline), 5-methyl-1H-1,6-naphthyridin-2-one (medorinone), 6-[4-(1-cyclohexyltetrazol-5-yl)butoxy]-3,4-dihydro-1H-quinolin-2-one (cilostazol), 2-[[2-[bis(2-hydroxyethyl)amino]-4,8-di(piperidin-1-yl)pyrimido[5,4-d]pyrimidin-6-yl]-(2-hydroxyethyl)amino]ethanol (dipyridamole), 3-amino-5-pyridin-4-yl-1H-pyridin-2-one (amrinone), 1-butyl-3-(4-methylphenyl)sulfonylurea (tolbutamide), 1,3-dimethyl-7H-purine-2,6-dione (theophylline) and 3,7-dimethyl-1-(5-oxohexyl)purine-2,6-dione (pentoxifylline) for use in inhibiting follicle maturation, such as for use in inhibiting the primordial to primary transition of follicles.

Carbamoyl-Phosphate Synthase 1 as a Target

In another aspect, the present invention relates to a compound for use in regulating follicle maturation, wherein said compound can regulate the activity of Carbamoyl-Phosphate Synthase 1 (CPS1).

CPS1 was found to be significantly consistently expressed in primary oocytes and significantly downregulated in primary oocytes when compared to primordial oocytes.

In one embodiment inhibition of CPS1 inhibits follicle maturation. Thus, preferably, said compound is an inhibitor of CPS1. In another preferred embodiment, said compound or said inhibitor inhibits follicle maturation. In a preferred embodiment said compound or inhibitor of CPS1 regulates the primordial to primary transition of follicles. In a particular preferred embodiment said compound or said inhibitor of CPS1 inhibits the primordial to primary transition of follicles.

In a particular embodiment, said compound or said inhibitor is ((2S)-2-(carbamoylamino)pentanedioic acid (N-Carbamyl-L-glutamic acid).

Thus, a preferred embodiment of the present invention relates to N-Carbamyl-L-glutamic acid for use in regulating follicle maturation, such as for use in regulating the primordial to primary transition of follicles. A particular preferred embodiment relates to N-Carbamyl-L-glutamic acid for use in inhibiting follicle maturation, such as for use in inhibiting the primordial to primary transition of follicles.

Nuclear Factor Erythroid 2 Like 2 as a Target

Yet another aspect of the present invention relates to a compound for use in regulating follicle maturation, wherein said compound can regulate the activity of Nuclear Factor Erythroid 2 Like 2 (NFE2L2).

NFE2L2 was found to be significantly consistently expressed in primary oocytes.

In addition, it was found that regulation of NFE2L2 results in a regulation of follicle maturation. More specifically, inhibition of NFE2L2 promotes follicle maturation.

Thus, in a preferred embodiment, said compound is an inhibitor of NFE2L2. In another preferred embodiment, said compound or said inhibitor promotes follicle maturation. In a preferred embodiment said compound or inhibitor of NFE2L2 regulates the primordial to primary transition of follicles. In a particular preferred embodiment said compound or inhibitor of NFE2L2 promotes the primordial to primary transition of follicles.

In a particular embodiment, said compound or said inhibitor is 1-methylpyridin-1-ium-3-carboxylic acid; chloride (Trigonellin hydrochloride). Trigonellin hydrochloride is an inhibitor of NFE2L2.

Thus, a preferred embodiment of the present invention relates to Trigonellin hydrochloride for use in regulating follicle maturation, such as for use in regulating the primordial to primary transition of follicles. A particular preferred embodiment relates to Trigonellin hydrochloride for use in promoting follicle maturation, such as for use in promoting the primordial to primary transition of follicles.

Protein Tyrosine Kinase 2 Beta as a Target

One aspect of the present invention relates to a compound for use in regulating follicle maturation, wherein said compound can regulate the activity of Protein Tyrosine Kinase 2 Beta (PTK2B).

PTK2B was found to be significantly consistently expressed in primordial oocytes and in primary oocytes.

In one embodiment inhibition of PTK2B inhibits follicle maturation. Thus, preferably, said compound is an inhibitor of PTK2B. In another preferred embodiment, said compound or said inhibitor inhibits follicle maturation. In a preferred embodiment said compound or inhibitor of PTK2B regulates the primordial to primary transition of follicles. In a particular preferred embodiment said compound or said inhibitor of PTK2B inhibits the primordial to primary transition of follicles.

In one embodiment said compound or said inhibitor is selected from the group consisting of N-methyl-N-[3-[[[2-[(2-oxo-1,3-dihydroindol-5-yl)amino]-5-(trifluoromethyl) pyrimidin-4-yl]amino]methyl]pyridin-2-yl]methanesulfonamide (PF-562271) and CT-707. These compounds are inhibitors of PTK2B.

Thus, a preferred embodiment of the present invention relates to a compound or an inhibitor selected from the group consisting of N-methyl-N-[3-[[[2-[(2-oxo-1,3-dihydroindol-5-yl)amino]-5-(trifluoromethyl)pyrimidin-4-yl]amino] methyl]pyridin-2-yl]methanesulfonamide (PF-562271) and CT-707 for use in regulating follicle maturation, such as for use in regulating the primordial to primary transition of follicles.

A particular preferred embodiment relates to a compound or an inhibitor selected from the group consisting of N-methyl-N-[3-[[[2-[(2-oxo-1,3-dihydroindol-5-yl)amino]-5-(trifluoromethyl)pyrimidin-4-yl]amino]methyl]pyridin-2-yl]methanesulfonamide (PF-562271) and CT-707 for use in inhibiting follicle maturation, such as for use in inhibiting the primordial to primary transition of follicles.

Mouse Double Minute 2 Homolog

In a further aspect, the present invention relates to a compound for use in regulating follicle maturation, wherein said compound can regulate the activity of Mouse double minute 2 homolog (MDM2). MDM2 is also known as E3 ubiquitin-protein ligase Mdm2.

MDM2 was found to be significantly consistently expressed in primary oocytes.

In one embodiment inhibition of MDM2 promotes follicle maturation. Thus, preferably, said compound is an inhibitor of MDM2. In another preferred embodiment, said compound or said inhibitor promotes follicle maturation. In a preferred embodiment said compound or inhibitor of MDM2 regulates the primordial to primary transition of follicles. In a particular preferred embodiment said compound or said inhibitor of MDM2 promotes the primordial to primary transition of follicles.

In a particular preferred embodiment said compound or said inhibitor is selected from the group consisting of 1-N-[2-(1H-indol-3-yl)ethyl]-4-N-pyridin-4-ylbenzene-1,4-diamine (serdemetan), (1S)-1-(4-chlorophenyl)-6-methoxy-2-[4-[methyl-[[4-(4-methyl-3-oxopiperazin-1-yl)cyclohexyl]methyl]amino]phenyl]-7-propan-2-yloxy-1,4-dihydroisoquinolin-3-one (CGM097), L-Erythro-hexonamide, 2,6-anhydro-5-((((3'R,4'S,5'R)-6"-chloro-4'-(2-chloro-3-fluoro-4-pyridinyl)-1",2"-dihydro-4,4-dimethyl-2"-oxodispiro(cyclohexane-1,2'-pyrrolidine-3',3"-(3H)indol)-5'-yl)carbonyl)amino)-3,4,5-trideoxy-, 4-methylbenzenesulfon (DS-3032b), 4-amino-1-[(2R,3S,4S,5R)-3,4-dihydroxy-5-(hydroxymethyl)oxolan-2-yl]pyrimidin-2-one (MK-8242), (6S)-5-(5-chloro-1,2-dihydro-1-methyl-2-oxo-3-pyridinyl)-6-(4-chlorophenyl)-2-(2,4-dimethoxy-5-pyrimidinyl)-5,6-dihydro-1-(1-methylethyl)-Pyrrolo[3,4-d]imidazol-4(1H)-one (HDM201), ALRN-6924, 4-{[(3S,4R,5S)-3-(3-Chloro-2-fluorophenyl)-4-(4-chloro-2-fluorophenyl)-4-cyano-5-(2,2-dimethylpropyl)-D-prolyl]amino}-3-methoxybenzoic acid (idasanutlin), RO6839921, [(4S,5R)-2-(4-tert-butyl-2-ethoxyphenyl)-4,5-bis(4-chlorophenyl)-4,5-dimethylimidazol-1-yl]-[4-(3-methylsulfonylpropyl)piperazin-1-yl]methanone (RO-5045337), 2-[(3R,5R,6S)-5-(3-chlorophenyl)-6-(4-chlorophenyl)-3-methyl-1-[(2S)-3-methyl-1-propan-2-ylsulfonylbutan-2-yl]-2-oxopiperidin-3-yl]acetic acid (AMG-232) and APG-115. These compounds are inhibitors of MDM2.

Thus, a preferred embodiment of the present invention relates to a compound or an inhibitor selected from the group consisting of 1-N-[2-(1H-indol-3-yl)ethyl]-4-N-pyridin-4-ylbenzene-1,4-diamine (serdemetan), (1S)-1-(4-chlorophenyl)-6-methoxy-2-[4-[methyl-[[4-(4-methyl-3-oxopiperazin-1-yl)cyclohexyl]methyl]amino]phenyl]-7-propan-2-yloxy-1,4-dihydroisoquinolin-3-one (CGM097), L-Erythro-hexonamide, 2,6-anhydro-5-((((3'R,4'S,5'R)-6"-chloro-4'-(2-chloro-3-fluoro-4-pyridinyl)-1",2"-dihydro-4,4-dimethyl-2"-oxodispiro(cyclohexane-1,2'-pyrrolidine-3',3"-(3H)indol)-5'-yl)carbonyl)amino)-3,4,5-trideoxy-, 4-methylbenzenesulfon (DS-3032b), 4-amino-1-[(2R,3S,4S,5R)-3,4-dihydroxy-5-(hydroxymethyl)oxolan-2-yl]pyrimidin-2-one (MK-8242), (6S)-5-(5-chloro-1,2-dihydro-1-methyl-2-oxo-3-pyridinyl)-6-(4-chlorophenyl)-2-(2,4-dimethoxy-5-pyrimidinyl)-5,6-dihydro-1-(1-methylethyl)-Pyrrolo[3,4-d]imidazol-4(1H)-one (HDM201), ALRN-6924, 4-{[(3S,4R,5S)-3-(3-Chloro-2-fluorophenyl)-4-(4-chloro-2-fluorophenyl)-4-cyano-5-(2,2-dimethylpropyl)-D-prolyl]amino}-3-methoxybenzoic acid (idasanutlin), RO6839921, [(4S,5R)-2-(4-tert-butyl-2-ethoxyphenyl)-4,5-bis(4-chlorophenyl)-4,5-dimethylimidazol-1-yl]-[4-(3-methylsulfonylpropyl)piperazin-1-yl]methanone (RO-5045337), 2-[(3R,5R,6S)-5-(3-chlorophenyl)-6-(4-chlorophenyl)-3-methyl-1-[(2S)-3-methyl-1-propan-2-ylsulfonylbutan-2-yl]-2-oxopiperidin-3-yl]acetic acid (AMG-232) and APG-115 for use in regulating follicle maturation, such as for use in regulating the primordial to primary transition of follicles.

A particular preferred embodiment relates to a compound or an inhibitor selected from the group consisting of 1-N-[2-(1H-indol-3-yl)ethyl]-4-N-pyridin-4-ylbenzene-1,4-diamine (serdemetan), (1S)-1-(4-chlorophenyl)-6-methoxy-2-[4-[methyl-[[4-(4-methyl-3-oxopiperazin-1-yl)cyclohexyl] methyl]amino]phenyl]-7-propan-2-yloxy-1,4-dihydroisoquinolin-3-one (CGM097), L-Erythro-hexonamide, 2,6-anhydro-5-((((3'R,4'S,5'R)-6"-chloro-4'-(2-chloro-3-fluoro-4-pyridinyl)-1",2"-dihydro-4,4-dimethyl-2"-oxodispiro(cyclohexane-1,2'-pyrrolidine-3',3"-(3H)indol)-5'-yl)carbonyl)amino)-3,4,5-trideoxy-, 4-methylbenzenesulfon (DS-3032b), 4-amino-1-[(2R,3S,4S,5R)-3,4-dihydroxy-5-(hydroxymethyl)oxolan-2-yl]pyrimidin-2-one (MK-8242), (6S)-5-(5-chloro-1,2-dihydro-1-methyl-2-oxo-3-pyridinyl)-6-(4-chlorophenyl)-2-(2,4-dimethoxy-5-pyrimidinyl)-5,6-dihydro-1-(1-methylethyl)-Pyrrolo[3,4-d]imidazol-4(1H)-one (HDM201), ALRN-6924, 4-{[(3S,4R,5S)-3-(3-Chloro-2-fluorophenyl)-4-(4-chloro-2-fluorophenyl)-4-cyano-5-(2,2-dimethylpropyl)-D- prolyl]amino}-3-methoxybenzoic acid (idasanutlin), RO6839921, [(4S,5R)-2-(4-tert-butyl-2-ethoxyphenyl)-4,5-bis(4-chlorophenyl)-4,5-dimethylimidazol-1-yl]-[4-(3-methylsulfonylpropyl)piperazin-1-yl]methanone (RO-5045337), 2-[(3R,5R,6S)-5-(3-chlorophenyl)-6-(4-chlorophenyl)-3-methyl-1-[(2S)-3-methyl-1-propan-2-ylsulfonylbutan-2-yl]-2-oxopiperidin-3-yl]acetic acid (AMG-232) and APG-115 for use in promoting follicle maturation, such as for use in promoting the primordial to primary transition of follicles.

Erb-B2 Receptor Tyrosine Kinase 4 as a Target

In another aspect, the present invention relates to a compound for use in regulating follicle maturation, wherein said compound can regulate the activity of Erb-B2 Receptor Tyrosine Kinase 4 (ERBB4).

ERBB4 was found to be significantly consistently expressed in primary oocytes.

In one embodiment inhibition of ERBB4 inhibits follicle maturation. Thus, preferably, said compound is an inhibitor of ERBB4. In another preferred embodiment, said compound or said inhibitor inhibits follicle maturation. In a preferred embodiment said compound or inhibitor of ERBB4 regulates the primordial to primary transition of follicles. In a particular preferred embodiment said compound or said inhibitor of ERBB4 inhibits the primordial to primary transition of follicles.

In one particular embodiment said compound or said inhibitor is selected from the group consisting of [(3S)-morpholin-3-yl]methyl N-[4-[[1-[(3-fluorophenyl)methyl]indazol-5-yl]amino]-5-methylpyrrolo[2,1-f][1,2,4]triazin-6-yl]carbamate (BMS-599626), (E)-N-[4-(3-chloro-4-fluoroanilino)-7-[(3S)-oxolan-3-yl]oxyquinazolin-6-yl]-4-(dimethylamino)but-2-enamide (afatinib), N-[2-[2-(dimethylamino)ethyl-methylamino]-4-methoxy-5-[[4-(1-methylindol-3-yl)pyrimidin-2-yl]amino]phenyl]prop-2-enamide (osimertinib), 1-[4-[4-(3,4-dichloro-2-fluoroanilino)-7-methoxyquinazolin-6-yl]oxypiperidin-1-yl]prop-2-en-1-one (poziotinib), 4-methyl-N-[3-(4-methylimidazol-1-yl)-5-(trifluoromethyl)phenyl]-3-[(4-pyridin-3-ylpyrimidin-2-yl)amino]benzamide (pirotinib) and (E)-N-[4-(3-chloro-4-fluoroanilino)-3-cyano-7-ethoxy-quinolin-6-yl]-4-(dimethylamino)but-2-enamide (pelitinib). These compounds are inhibitors of ERBB4.

Thus, a preferred embodiment of the present invention relates to a compound or an inhibitor selected from the group consisting of [(3S)-morpholin-3-yl]methyl N-[4-[[1-[(3-fluorophenyl)methyl]indazol-5-yl]amino]-5-methylpyrrolo[2,1-f][1,2,4]triazin-6-yl]carbamate (BMS-599626), (E)-N-[4-(3-chloro-4-fluoroanilino)-7-[(3S)-oxolan-3-yl]oxyquinazolin-6-yl]-4-(dimethylamino)but-2-enamide (afatinib), N-[2-[2-(dimethylamino)ethyl-methylamino]-4-methoxy-5-[[4-(1-methylindol-3-yl)pyrimidin-2-yl]amino]phenyl]prop-2-enamide (osimertinib), 1-[4-[4-(3,4-dichloro-2-fluoroanilino)-7-methoxyquinazolin-6-yl]oxypiperidin-1-yl]prop-2-en-1-one (poziotinib), 4-methyl-N-[3-(4-methylimidazol-1-yl)-5-(trifluoromethyl)phenyl]-3-[(4-pyridin-3-ylpyrimidin-2-yl)amino]benzamide (pirotinib) and (E)-N-[4-(3-chloro-4-fluoroanilino)-3-cyano-7-ethoxyquinolin-6-yl]-4-(dimethylamino)but-2-enamide (pelitinib) for use in regulating follicle maturation, such as for use in regulating the primordial to primary transition of follicles.

A particular preferred embodiment relates to a compound or an inhibitor selected from the group consisting of [(3S)-morpholin-3-yl]methyl N-[4-[[1-[(3-fluorophenyl)methyl]indazol-5-yl]amino]-5-methylpyrrolo[2,1-f][1,2,4]triazin-6-yl]carbamate (BMS-599626), (E)-N-[4-(3-chloro-4-fluoroanilino)-7-[(3S)-oxolan-3-yl]oxyquinazolin-6-yl]-4-(dimethylamino)but-2-enamide (afatinib), N-[2-[2-(dimethylamino)ethyl-methylamino]-4-methoxy-5-[[4-(1-methylindol-3-yl)pyrimidin-2-yl]amino]phenyl]prop-2-enamide (osimertinib), 1-[4-[4-(3,4-dichloro-2-fluoroanilino)-7-methoxyquinazolin-6-yl]oxypiperidin-1-yl]prop-2-en-1-one (poziotinib), 4-methyl-N-[3-(4-methylimidazol-1-yl)-5-(trifluoromethyl)phenyl]-3-[(4-pyridin-3-ylpyrimidin-2-yl)amino]benzamide (pirotinib) and (E)-N-[4-(3-chloro-4-fluoroanilino)-3-cyano-7-ethoxy-quinolin-6-yl]-4-(dimethylamino)but-2-enamide (pelitinib) for use in inhibiting follicle maturation, such as for use in inhibiting the primordial to primary transition of follicles.

Dual Specificity Protein Kinase as a Target

Yet another aspect of the present invention relates to a compound for use in regulating primordial follicle development, wherein said compound can regulate the activity of Dual Specificity Protein Kinase (TKK).

TKK was found to be significantly consistently expressed in primary oocytes (see Table 2).

In one embodiment inhibition of TKK inhibits follicle maturation. Thus, preferably, said compound is an inhibitor of TKK. In another preferred embodiment, said compound or said inhibitor inhibits follicle maturation. In a preferred embodiment said compound or inhibitor of TKK regulates the primordial to primary transition of follicles. In a particular preferred embodiment said compound or said inhibitor of TKK inhibits the primordial to primary transition of follicles.

In one embodiment said compound or said inhibitor is methyl 2,6-dimethyl-5-nitro-4-[2-(trifluoromethyl)phenyl]-1,4-dihydropyridine-3-carboxylate. Methyl 2,6-dimethyl-5-nitro-4-[2-(trifluoromethyl)phenyl]-1,4-dihydropyridine-3-carboxylate is an inhibitor of TKK.

Thus, a preferred embodiment of the present invention relates to methyl 2,6-dimethyl-5-nitro-4-[2-(trifluoromethyl)phenyl]-1,4-dihydropyridine-3-carboxylate for use in regulating follicle maturation, such as for use in regulating the primordial to primary transition of follicles.

A particular preferred embodiment relates to methyl 2,6-dimethyl-5-nitro-4-[2-(trifluoromethyl)phenyl]-1,4-dihydropyridine-3-carboxylate for use in inhibiting follicle maturation, such as for use in inhibiting the primordial to primary transition of follicles.

B Lymphoid Tyrosine Kinase as a Target

A further aspect of the present invention relates to a compound for use in regulating primordial follicle development, wherein said compound can regulate the activity of B Lymphoid Tyrosine Kinase (BLK).

BLK was found to be significantly consistently expressed in primordial oocytes and the expression of BLK was downregulated in primary oocytes when compared to primordial oocytes.

In one embodiment inhibition of BLK inhibits follicle maturation. Thus, preferably, said compound is an inhibitor of BLK. In another preferred embodiment, said compound or said inhibitor inhibits follicle maturation. In a preferred embodiment said compound or inhibitor of BLK regulates the primordial to primary transition of follicles. In a particular preferred embodiment said compound or said inhibitor of BLK inhibits the primordial to primary transition of follicles.

In one embodiment said compound or said inhibitor is N-[2-[2-(dimethylamino)ethyl-methylamino]-4-methoxy-5-[[4-(1-methylindol-3-yl)pyrimidin-2-yl]amino]phenyl]prop-2-enamide (osimertinib). N-[2-[2-(dimethylamino)

ethyl-methylamino]-4-methoxy-5-[[4-(1-methylindol-3-yl) pyrimidin-2-yl]amino]phenyl]prop-2-enamide (osimertinib) is an inhibitor of TKK.

Thus, a preferred embodiment of the present invention relates to N-[2-[2-(dimethylamino)ethyl-methylamino]-4-methoxy-5-[[4-(1-methylindol-3-yl)pyrimidin-2-yl]amino] phenyl]prop-2-enamide (osimertinib) for use in regulating follicle maturation, such as for use in regulating the primordial to primary transition of follicles.

A particular preferred embodiment relates to N-[2-[2-(dimethylamino)ethyl-methylamino]-4-methoxy-5-[[4-(1-methylindol-3-yl)pyrimidin-2-yl]amino]phenyl]prop-2-enamide (osimertinib) for use in inhibiting follicle maturation, such as for use in inhibiting the primordial to primary transition of follicles.

Insulin Like Growth Factor 1 Receptor as a Target

Another aspect of the present invention relates to a compound for use in regulating follicle maturation, wherein said compound can regulate the activity of Insulin Like Growth Factor 1 Receptor (IGF1R).

IGF1R was found to be significantly consistently expressed in primordial oocytes and in primary oocytes.

In one embodiment inhibition of IGF1R inhibits follicle maturation. Thus, preferably, said compound is an inhibitor of IGF1R. In another preferred embodiment, said compound or said inhibitor inhibits follicle maturation. In a preferred embodiment said compound or inhibitor of IGF1R regulates the primordial to primary transition of follicles. In a particular preferred embodiment said compound or said inhibitor of BLK inhibits the primordial to primary transition of follicles.

In one embodiment said compound or said inhibitor is selected from the group consisting of (5R,5aR,8aS,9R)-5-hydroxy-9-(3,4,5-trimethoxyphenyl)-5a,6,8a,9-tetrahydro-5H-[2]benzofuro[5,6-f][1,3]benzodioxol-8-one (picropodophyllin), 3-[8-amino-1-(2-phenylquinolin-7-yl)imidazo[1,5-a]pyrazin-3-yl]-1-methylcyclobutan-1-ol)(LC Laboratories (linsitinib), cixutumumab, N-(2-chloro-6-methylphenyl)-2-[[6-[4-(2-hydroxyethyl)piperazin-1-yl]-2-methylpyrimidin-4-yl]amino]-1,3-thiazole-5-carboxamide (ganitumab), ((E)-N-[4-[3-chloro-4-(pyridin-2-ylmethoxy)anilino]-3-cyano-7-ethoxyquinolin-6-yl]-4-(dimethylamino)but-2-enamide (Neratinib), 4-N-(5-cyclopropyl-1H-pyrazol-3-yl)-6-(4-methylpiperazin-1-yl)-2-N-[(3-propan-2-yl-1,2-oxazol-5-yl)methyl]pyrimidine-2,4-diamine (XL228), 4-[4-[[4-chloro-3-(trifluoromethyl)phenyl]carbamoylamino] phenoxy]-N-methyl-pyridine-2-carboxamide (BIIB022), 4-amino-N-(1-azabicyclo[3.3.1]nonan-4-yl)-5-chloro-2-methoxybenzamide) (dalotuzumab) and MM-141. These compounds are inhibitors of BLK.

Cixutumumab (IMC-A12) is a human monoclonal antibody normally used for the treatment of solid tumors. It is a fully human IgG1 monoclonal antibody directed against the human insulin-like growth factor-1 receptor (IGF-1R) with potential antineoplastic activity. Cixutumumab selectively binds to membrane-bound IGF-1R, thereby preventing the binding of the ligand IGF-1 and subsequent activation of PI3K/AKT signaling pathway.

Thus, a preferred embodiment of the present invention relates to a compound or an inhibitor is selected from the group consisting of (5R,5aR,8aS,9R)-5-hydroxy-9-(3,4,5-trimethoxyphenyl)-5a,6,8a,9-tetrahydro-5H-[2]benzofuro [5,6-f][1,3]benzodioxol-8-one (picropodophyllin), 3-[8-amino-1-(2-phenylquinolin-7-yl)imidazo[1,5-a]pyrazin-3-yl]-1-methylcyclobutan-1-ol)(LC Laboratories (linsitinib), cixutumumab, N-(2-chloro-6-methylphenyl)-2-[[6-[4-(2-hydroxyethyl)piperazin-1-yl]-2-methylpyrimidin-4-yl] amino]-1,3-thiazole-5-carboxamide (ganitumab), ((E)-N-[4-[3-chloro-4-(pyridin-2-ylmethoxy)anilino]-3-cyano-7-ethoxyquinolin-6-yl]-4-(dimethylamino)but-2-enamide (Neratinib), 4-N-(5-cyclopropyl-1H-pyrazol-3-yl)-6-(4-methylpiperazin-1-yl)-2-N-[(3-propan-2-yl-1,2-oxazol-5-yl)methyl]pyrimidine-2,4-diamine (XL228), 4-[4-[[4-chloro-3-(trifluoromethyl)phenyl]carbamoylamino] phenoxy]-N-methyl-pyridine-2-carboxamide (BIIB022), 4-amino-N-(1-azabicyclo[3.3.1]nonan-4-yl)-5-chloro-2-methoxybenzamide) (dalotuzumab) and MM-141 for use in regulating follicle maturation, such as for use in regulating the primordial to primary transition of follicles.

A particular preferred embodiment relates to a compound or an inhibitor is selected from the group consisting of (5R,5aR,8aS,9R)-5-hydroxy-9-(3,4,5-trimethoxyphenyl)-5a,6,8a,9-tetrahydro-5H-[2]benzofuro[5,6-f][1,3]benzodioxol-8-one (picropodophyllin), 3-[8-amino-1-(2-phenylquinolin-7-yl)imidazo[1,5-a]pyrazin-3-yl]-1-methylcyclobutan-1-ol)(LC Laboratories (linsitinib), cixutumumab, N-(2-chloro-6-methylphenyl)-2-[[6-[4-(2-hydroxyethyl)piperazin-1-yl]-2-methylpyrimidin-4-yl] amino]-1,3-thiazole-5-carboxamide (ganitumab), ((E)-N-[4-[3-chloro-4-(pyridin-2-ylmethoxy)anilino]-3-cyano-7-ethoxyquinolin-6-yl]-4-(dimethylamino)but-2-enamide (Neratinib), 4-N-(5-cyclopropyl-1H-pyrazol-3-yl)-6-(4-methylpiperazin-1-yl)-2-N-[(3-propan-2-yl-1,2-oxazol-5-yl)methyl]pyrimidine-2,4-diamine (XL228), 4-[4-[[4-chloro-3-(trifluoromethyl)phenyl]carbamoylamino] phenoxy]-N-methyl-pyridine-2-carboxamide (BIIB022), 4-amino-N-(1-azabicyclo[3.3.1]nonan-4-yl)-5-chloro-2-methoxybenzamide) (dalotuzumab) and MM-141 for use in inhibiting follicle maturation, such as for use in inhibiting the primordial to primary transition of follicles.

MM-141 is also known as istiratumab. MM-141 is a tetravalent bispecific antibody targeting insulin-like growth factor 1 (IGF-1) receptor (IGF1R; CD221) and Erb-b2 receptor tyrosine kinase 3 (ERBB3; HER3; EGFR3).

Insulin Like Growth Factor 2 as a Target

Yet another aspect of the present invention relates to a compound for use in regulating follicle maturation, wherein said compound can regulate the activity of Insulin Like Growth Factor 2 (IGF2).

IGF2 was found to be significantly consistently expressed in primary oocytes.

In one embodiment inhibition of IGF2 inhibits follicle maturation. Thus, preferably, said compound is an inhibitor of IGF2. In another preferred embodiment, said compound or said inhibitor inhibits follicle maturation. In a preferred embodiment said compound or inhibitor of IGF2 regulates the primordial to primary transition of follicles. In a particular preferred embodiment said compound or said inhibitor of IGF2 inhibits the primordial to primary transition of follicles.

In one embodiment said compound or said inhibitor is BI 836845. BI 836845 is an antibody that binds to and inhibits IGF2.

BI 836845 is also known as Xentuzumab. Xentuzumab is a humanised immunoglobulin G1 (IgG1) monoclonal antibody that binds to and neutralises the function of human insulin-like growth factor-1 and 2 (IGF-1, IGF-2). This results in effective inhibition of IGF-induced activation of both IGF-IR and IR-A (Friedbichler K, et al., Mol Cancer Ther 2014; 13(2):399-409).

Thus, a preferred embodiment of the present invention relates BI 836845 for use in regulating follicle maturation, such as for use in regulating the primordial to primary transition of follicles.

A particular preferred embodiment relates to BI 836845 for use in inhibiting follicle maturation, such as for use in inhibiting the primordial to primary transition of follicles.

Use of the Compounds According to the Present Invention

The compounds according to the present invention can be used in vivo wherein they are administered to a female individual in need thereof. Thus, in one embodiment the compounds as described herein and above are for use in regulating follicle maturation in vivo.

The compounds can also be used in vitro wherein they are added in vitro to follicles. Thus, in another embodiment the compounds as described herein and above are for use in regulating follicle maturation in vitro.

In a preferred embodiment of the present invention the compounds as described herein and above are for use in regulating primordial to primary transition of follicles. Thus, an aspect of the present invention relates to a compound as defined herein and above for use in regulating primordial to primary transition of follicles.

In a preferred embodiment said follicles are mammalian follicles. The mammalian can be any mammal such as for example a rodent, a primate, or a carnivore. In a preferred embodiment the rodent is a mouse.

In a preferred embodiment, the mammalian is a human female.

The compounds as defined herein and above can be used to exert pharmacological control of follicle regulation, in particular primordial to primary follicle regulation.

Several diseases or disorders are associated with poor control in the first step of follicle regulation, namely primordial to primary follicle regulation. These disorders are commonly referred to as ovulation disorders. Problems with the regulation of reproductive hormones by the hypothalamus or the pituitary gland, or problems in the ovary, can cause ovulation disorders.

Thus, a further aspect of the present invention relates to a compound as described and defined herein and above for use in treating, preventing or ameliorating infertility or reduced fertility.

For example, the present invention relates to a compound as described and defined herein and above for use in treating, preventing or ameliorating infertility or reduced fertility in a female mammal.

Preferably said female individual is a female mammal. The mammal is as defined above. Thus, preferably, said female mammal is a female human.

An aspect of the present invention relates to a compound as described and defined herein and above for use in treating, preventing or ameliorating an ovulation disorder, such as an ovulation disorder.

In one embodiment said ovulation disorder is an infertility disorder.

In one embodiment said ovulation disorder is selected from the group consisting of Polycystic ovary syndrome (PCOS), Premature ovarian failure (P01), Hypothalamic dysfunction and Menopause.

PCOS causes a hormone imbalance, which affects ovulation (amongst other, it an endoctien metabolic disease). PCOS is a condition that causes women to not ovulate, or to ovulate irregularly. PCOS is associated with insulin resistance and obesity, abnormal hair growth on the face or body, and acne. PCOS is the most common cause of female infertility.

Premature ovarian failure (P01), also called primary ovarian insufficiency, is a disorder usually caused by an autoimmune response or by premature loss of eggs from your ovary (possibly from genetics or chemotherapy). POI, sometimes referred to as premature menopause, occurs when a woman's ovaries fail before she is 40 years of age The ovary no longer produces eggs, and it lowers estrogen production in women under the age of 40. Although certain exposures, such as chemotherapy or pelvic radiation therapy, and certain medical conditions may cause POI, the cause is often unexplained.

Hypothalamic dysfunction also called Functional hypothalamic amenorrhea (FHA) is a condition caused by excessive exercise, stress, or low body weight. It is sometimes associated with eating disorders such as anorexia. Two hormones produced by the pituitary gland are responsible for stimulating ovulation each month—(FSH) and luteinizing hormone (LH). Excess physical or emotional stress, a very high or very low body weight, or a recent substantial weight gain or loss can disrupt production of these hormones and affect ovulation. Irregular or absent periods are the most common signs.

The ovulation disorder may also be caused by hyperprolactinemia, wherein too much prolactin is produced. For example, the pituitary gland may cause excess production of prolactin (hyperprolactinemia), which reduces estrogen production and may cause infertility. Usually related to a pituitary gland problem, this can also be caused by medications you're taking for another disease.

In another embodiment the ovulation disorder is caused by improper function of the hypothalamus and pituitary glands. The hypothalamus and pituitary glands in the brain produce hormones that maintain normal ovarian function. Production of too much of the hormone prolactin by the pituitary gland (often as the result of a benign pituitary gland tumor), or improper function of the hypothalamus or pituitary gland, may cause a woman not to ovulate.

Pharmaceutical Formulation

Whilst it is possible for the compounds of the present invention to be administered alone, it is preferred to present them in the form of a pharmaceutical formulation.

Thus, another aspect of the present invention relates to a pharmaceutical composition comprising at least one compound as defined herein for use in treating, preventing or ameliorating ameliorating infertility or reduced fertility.

For example, the present invention relates to a pharmaceutical composition comprising at least one compound as defined herein for use in treating, preventing or ameliorating infertility or reduced fertility in a female mammal.

Preferably said female individual is a female mammal. The mammal is as defined above. Thus, preferably, said female mammal is a female human.

An aspect of the present invention relates to a pharmaceutical composition comprising at least one compound as defined herein for use in treating, preventing or ameliorating an ovulation disorder, such as an infertility disorder.

The ovulation disorder is as described herein and above.

It is preferred that the pharmaceutical composition further comprises at least one pharmaceutically acceptable carrier. Suitable carriers and the formulation of such pharmaceuticals are known to a person skilled in the art.

The pharmaceutically acceptable carriers can be either solid or liquid. Solid form preparations include powders, tablets, pills, capsules, cachets, suppositories, and dispersible granules. A solid carrier can be one or more excipients which may also act as diluents, flavoring agents, solubilizers, lubricants, suspending agents, binders, preservatives, wetting agents, tablet disintegrating agents, or an encapsulating material.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The compounds of the present invention may be formulated for parenteral administration and may be presented in unit dose form in ampoules, pre-filled syringes, small volume infusion or in multi-dose containers, optionally with an added preservative. The compositions may take such forms as suspensions, solutions, or emulsions in oily or aqueous vehicles, for example solutions in aqueous polyethylene glycol. Examples of oily or non-aqueous carriers, diluents, solvents or vehicles include propylene glycol, polyethylene glycol, vegetable oils (e.g., olive oil), and injectable organic esters (e.g., ethyl oleate), and may contain agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

Preferably, the formulation will comprise about 0.5% to 75% by weight of the active ingredient(s) with the remainder consisting of suitable pharmaceutical excipients as described herein.

Pharmaceutically acceptable salts of the instant compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

The compounds of the present invention may be formulated in a wide variety of formulations for parenteral administration.

For injections and infusions the formulations may take such forms as suspensions, solutions, or emulsions in oily or aqueous vehicles, for example solutions in aqueous polyethylene glycol. Alternatively, the active ingredient may be in powder form, obtained by aseptic isolation of sterile solid or by lyophilisation from solution for constitution before use with a suitable vehicle, e.g., sterile, pyrogen-free water. The formulations can be presented in unit-dose or multi-dose sealed containers, such as ampoules, vials, pre-filled syringes, infusion bags, or can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Examples of oily or non-aqueous carriers, diluents, solvents or vehicles include propylene glycol, polyethylene glycol, vegetable oils, and injectable organic esters, and may contain formulatory agents such as preserving, wetting, emulsifying or suspending, stabilizing and/or dispersing agents.

The formulations for injection will typically contain from about 0.5 to about 25% by weight of the active ingredient in solution.

The compounds of the present invention may be formulated in a wide variety of formulations for oral administration. Solid form preparations may include powders, tablets, drops, capsules, cachets, lozenges, and dispersible granules. Other forms suitable for oral administration may include liquid form preparations including emulsions, syrups, elixirs, aqueous solutions, aqueous suspensions, or solid form preparations which are intended to be converted shortly before use to liquid form preparations, such as solutions, suspensions, and emulsions.

In powders, the carrier is a finely divided solid which is a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. Suitable solvents for the preparation of an oily solution include glycerol, diluted alcohol and propylene glycol.

Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well-known suspending agents.

In one embodiment the pharmaceutical composition comprises an additional active agent. The pharmaceutical composition may also comprise a combination of the compounds as described herein and above.

Administration Forms

As described herein above administration forms include but are not limited to oral, parental, enteral, rectal or buccal administration.

In one embodiment the pharmaceutical composition is administered or adapted for administration enterally, parenterally or as part of a sustained release implant. The parenteral administration may for example be intravenous, subcutaneous, intramuscular, intracranial or intraperitoneal.

In a preferred embodiment the pharmaceutical composition is administered by or adapted for injection. In a preferred embodiment the pharmaceutical composition is administered by or adapted for injection into the ovaries.

It is appreciated that the pharmaceutical composition of the present invention comprises at least 30 wt. % compound, such as at least 25 wt. % compound, such as for example at least 20 wt. % compound, at least 15 wt. % compound, such as at least 25 wt. % compound, such as for example at least 20 wt. % compound, at least 15 wt. % compound, such as at least 10 wt. % compound, such as for example at least 8 wt. % compound, at least 5 wt. % compound, such as at least 4 wt. % compound, such as for example at least 3 wt. % compound, at least 2 wt. % compound, such as at least 1 wt. % compound, such as for example at least 0.5 wt. % compound or at least 0.5 wt. % compound.

Wt. % is an abbreviation for weight percent. The compound is any compound defined herein.

In one embodiment the compound as described herein is to be administered in a dosage of from 1 μg/kg-30,000 μg/kg body weight, such as 1 μg/kg-7,500 μg/kg, such as 1 μg/kg-5,000 μg/kg, such as 1 μg/kg-2,000 μg/kg, such as 1 μg/kg-1,000 μg/kg, such as 1 μg/kg-700 μg/kg, such as 5 μg/kg-500 μg/kg, such as 10 μg/kg to 100 μg/kg bodyweight. In another embodiment the compound as described herein is to be administered in a dosage of from 1 μg/kg-1,000 μg/kg body weight, such as 1 μg/kg-500 μg/kg, such as 1 μg/kg-250 μg/kg, such as 1 μg/kg-100 μg/kg, such as 1 μg/kg-50 μg/kg, such as 1 μg/kg to 10 μg/kg bodyweight. In yet another embodiment the compound as described herein is to be administered in a dosage of from 10 μg/kg-30,000 μg/kg body weight, such as 10 μg/kg-7,500 μg/kg, such as 10 μg/kg-5,000 μg/kg, such as 10 μg/kg-2,000 μg/kg, such as 10 μg/kg-1,000 μg/kg, such as 10 μg/kg-700 μg/kg, such as 10 μg/kg-500 μg/kg, such as 10 μg/kg to 100 μg/kg bodyweight.

In one embodiment the administration of the pharmaceutical composition as described herein is repeated at least 1, 2, 3, 4, 5 or 6 times weekly. In another embodiment the administration is repeated at least 1-3 times weekly, such as 2-5 times weekly, such as 3-6 times weekly.

The pharmaceutical composition of the present invention may also be administered in vitro to primordial follicles from said female individual. Thus, primordial follicles can be taken from an individual in need thereof, treated in vitro with at least one compound of the present invention and re-inserted into said female individual.

In one embodiment said female individual is a female mammal. Preferably, said female mammal is a female human.

Methods

A further aspect of the present invention relates to a method for treating, preventing or ameliorating infertility of a female individual having an ovulation disorder, comprising administering to said individual a therapeutically effective amount of a compound as defined herein and above.

The compound may also be administered in the form of a pharmaceutical composition as described herein and above. Administrations forms and dosages are as described herein and above.

The ovulation disorder is as described herein and above. In one embodiment said ovulation disorder is an infertility disorder.

Preferably, said female individual is a female mammal, such as a female human.

EXAMPLES

Materials and Methods

Participants

Oocyte samples were obtained from ovarian cortical tissue procured from three patients who underwent unilateral oophorectomy prior to gonadotoxic treatment for a malignant disease (unrelated to any ovarian malignancies). Patients were normo-ovulatory, with normal reproductive hormones, and had not received ovarian stimulation with exogenous gonadotropins. All procedures were carried out in accordance with relevant guidelines and regulations, and The Central Denmark Region Committees on Biomedical Research Ethics and the Danish Data Protection Agency approved the study. Written informed consent was obtained from all participants before inclusion. Patients consented to the research conducted. In subjects undergoing oophorectomy, a small piece of the ovarian cortex is used for evaluating the ovarian reserve and for research purposes. Ovarian cortical tissue, collected at a random time point in the menstrual cycle, was cryopreserved and catagorised the tissue as normal by morphological assessment (Rosendahl et al., 2011). Following cryopreservation, one small piece of ovarian cortex from each patient was randomly chosen for the current study. Until use, the cortical sample was stored in liquid nitrogen (−196° C.), as previously described (Andersen et al., 2008).

Laser Capture Micro-Dissection (LCM).

From each of the three patients, the following types of isolation were made a) pools of pure primordial oocytes, and b) pools of pure primary oocytes.

Details on RNA isolation, library preparation and sequencing, mapping and statistical analysis, bioinformatics, qPCR, and immunohistochemistry are available in Supplementary Information.

Results

Example 1

Identification of Candidates that are Involved in Follicle Development

Data Preparation and Filtration of Oocyte Transcriptome Data

Figure 2:
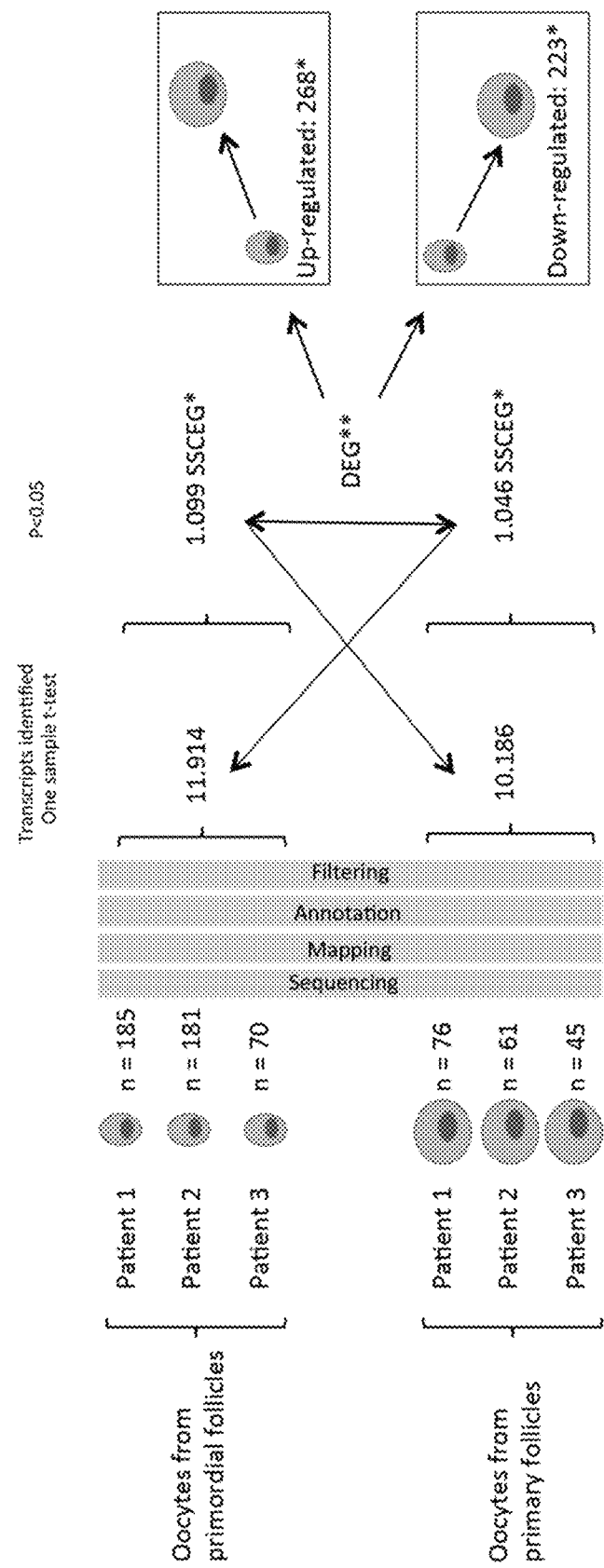
FIG. 2: Construction of SSCEG and DEG lists
After the sequencing, mapping, annotation and filtering, as illustrated in FIG. 1b, the genes (11914 and 10186 from oocytes from primordial and primary follicles, respectively) were filtered to include transcripts based on t-test, which selected only consistently expressed genes for each oocyte stage (1099 SSCEG and 1046 SSCEG from oocytes from primordial and primary follicles, respectively). From those SSCEG genes, DEG genes were identified (268 DEG up-regulated in oocytes from primordial follicles in comparison to oocytes from primary follicles and 223 DEG down-regulated in follicles from primordial to primary follicles). For DEG, paired t-test p<0.05 between two sets of triplicates and/or FPKM value fold-change>2

Follicles were precisely staged based on their morphology (FIG. 1A and FIG. 1B) and oocytes stringently excised using LCM, allowing the collection of pure oocytes from primordial (N=3 patients, n=436 oocytes) and primary (N=3 patients, n=182 oocytes) follicles, respectively. Collected LCM-samples were subsequently grouped into three main samples for each stage, making a total of six samples (two from each patient), prior to library preparation and RNA sequencing (FIG. 1C and FIG. 2). RNA sequencing generated on average 77 million reads per sample (range: 64-110 million reads) that was mapped to the Human Genome (hg19) (average mapping: 35 million reads, range: 23-65 million reads), using RefSeq genes as template.

Sorting and Enrichment Analysis of RNA Sequencing Data from Oocytes from Primordial and Primary Follicles A total of 1099 transcripts were found significantly expressed in oocytes from primordial follicles (Table 1, FIG. 2), and 1046 transcripts were found significantly expressed in oocytes from primary follicles (Table 2, FIG. 2). Using a stringent one-sample t-test (p<0.05) as statistical cut off, a list of SSCEG was generated for oocytes from primordial and primary follicles, respectively, and selected for further analysis (FIG. 2). The SSCEG analysis revealed 1099 transcripts (9.22%) (oocytes from primordial follicles, and 1046 transcripts (10.27%) (oocytes from primary follicles, of the expressed genes that were significantly and consistently expressed in a stage-specific manner in oocytes from primordial and primary follicles, respectively (FIG. 2).

The SSCEG from oocytes from primordial (1099) and primary (1046) follicles were used to identify genes that were differentially expressed between the two groups. The DEG analysis identified 223 genes that were significantly down-regulated during the transition of oocytes from primordial to primary (highest expression in oocytes from primordial follicles), and 268 genes that were significantly up-regulated (highest expression in oocytes from primary follicles) (FIG. 2).

A heatmap of DEG FPKM data was generated to show the expression for the two different cell-stages in isolates—and the correlation between stage-specific triplicate isolates.

The specific identity of the LCM-isolated oocytes was evaluated by the presence of a number of oocyte-specific transcripts, and the absence (or low, inconsistent presence) of granulosa cell-specific transcripts.

The continued IPA® generated enrichment analysis of the transcriptomes was performed on the following four groups.

1) SSCEG in oocytes from primordial follicles (1099 genes) 2) SSCEG in oocytes from primary follicles (1046 genes). 3) DEG down-regulated (223) or 4) DEG up-regulated (268) in oocytes during the primordial-to-primary follicle transition (FIG. 2).

The IPA® software was employed to perform the enrichment analysis. In this enrichment analysis, three Biological System groups were selected to analyse the transcriptomes; 1) 'Canonical Pathways' 2) 'Molecular and Cellular Functions' and 3) 'Biological Networks', and only significant ($p<0.05$) enrichments are included in the text.

Based on the transcriptome data the candidates mentioned in tables 1 a or 2 were identified as candidates for use in regulating follicle development by adding a compound that changes the activity of the candidate and determining whether said compound was capable of regulating follicle maturation, in particular regulating the primordial to primary transitions of follicles.

TABLE 1

Figure 4:
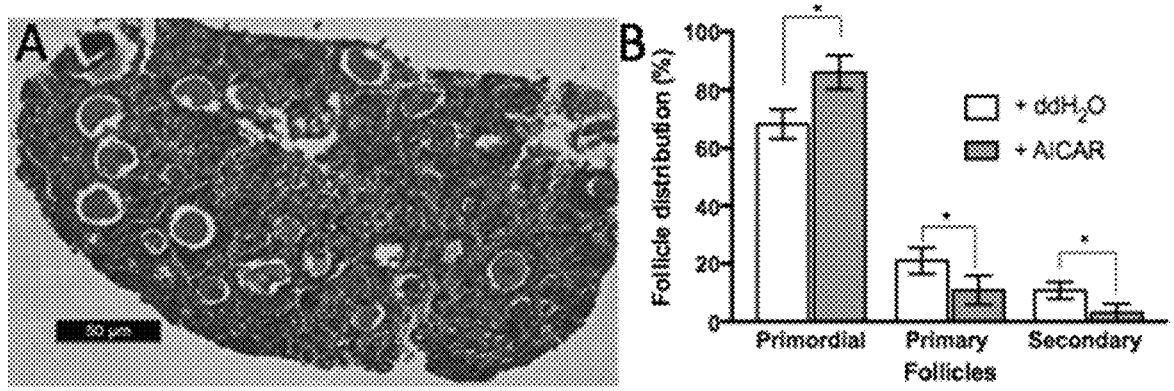
FIG. 4: Ovaries treated with the AMPK activator AICAR. (A) H&E dyed paraffin section of a juvenile mouse ovary after 4-day of culture with 1 mM AICAR. (B) Follicle distribution of ovaries incubated with AICAR or in control media (ddH$_2$O). Significant differences (P<0.05) are marked with an asterisks.
Figure 5:
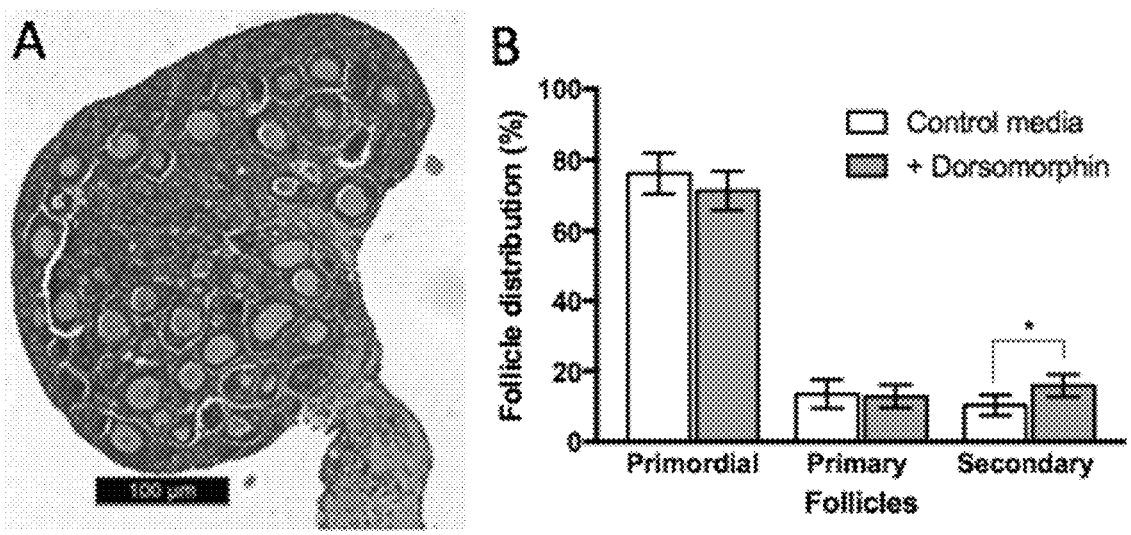
FIG. 5: Ovaries treated with AMPK inhibitor dorsomorphin. (A) H&E stained paraffin sections of juvenile ovaries after 4-day organ culture with dorsomorphin. (B) Follicle distribution of ovaries incubated with dorsomorphin or in control media. Significant differences (P<0.05) are marked with an asterisk.
Figure 8:
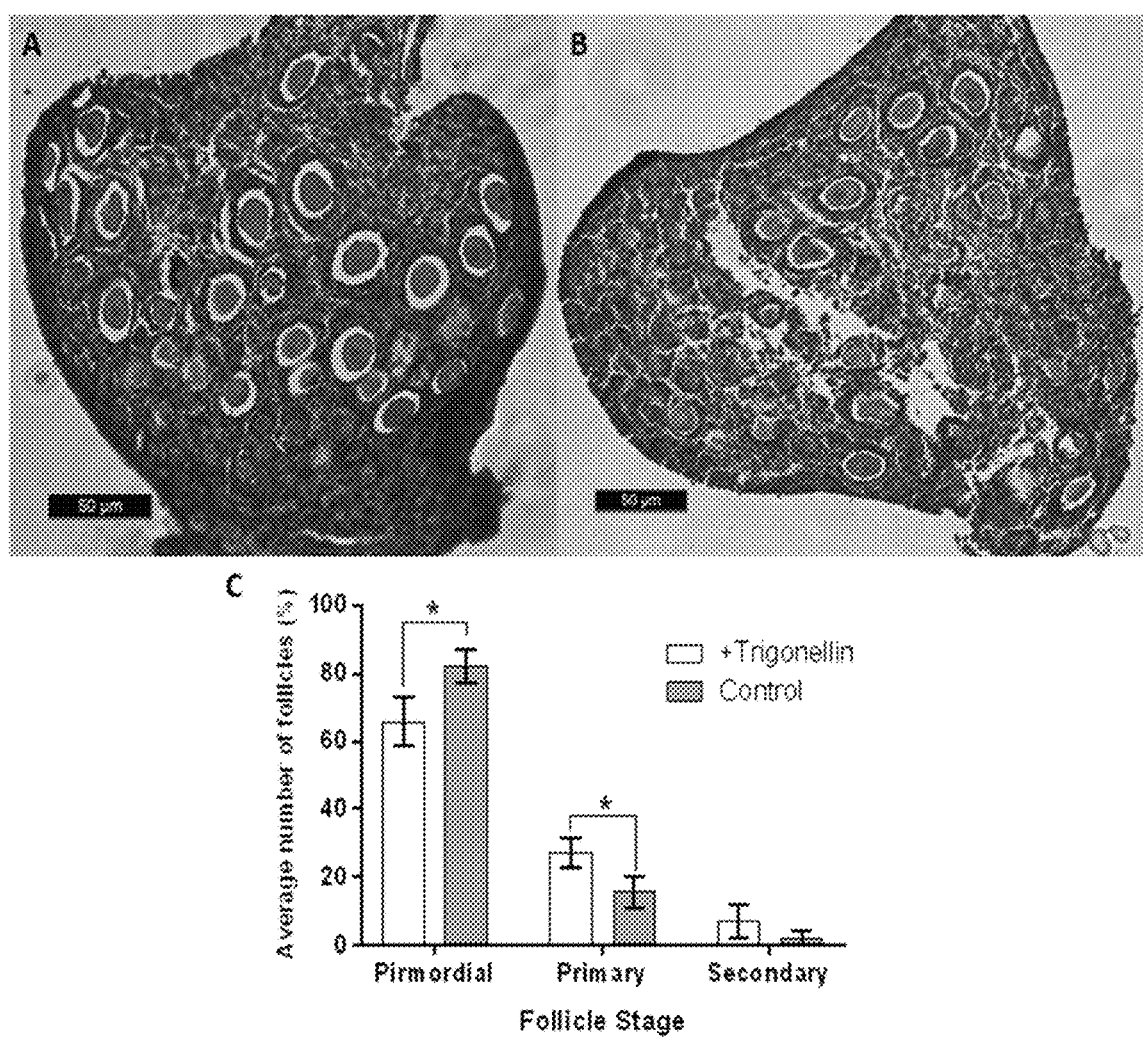
FIG. 8. The effect of the NFE2L2 inhibitor Trigonellin on follicle distribution. (A) H&E stained paraffin sections treated with 1.0 µM Trigonellin or (B) without (control). (C) Follicle distribution of ovaries incubated with Trigonellin or in control media. Three sections were counted for each treatment. The average number of follicles (%) is represented (±standard errors of the mean). Significant differences (P<0.05) are marked with an asterisk.
Figure 9:
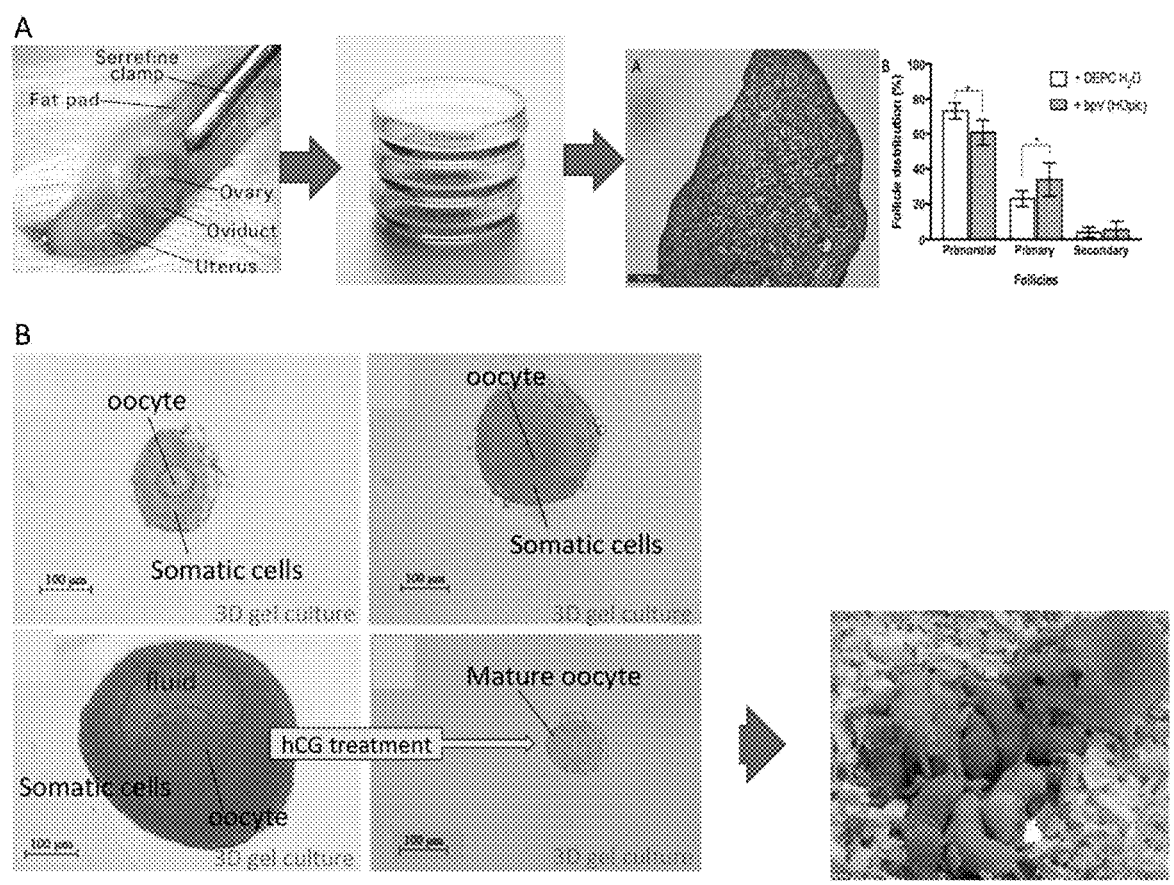
FIG. 9. (A) We use mouse ovarian culturing to screen for the effect of compounds, for their ability to induce or inhibit primordial follicle activation. (B) Once the effect is evaluated (as described in (A), single follicels will be compound-treated in gel-containing 3D culture (Amoushahi et al, unpublished), and the mature oocyte will be generated using human choridan gonadotrophin (hCG), prior to in vitro fertilization and transfer back into a female mouse. The ability to give birth to litters will be evaluated for each compound.

| Compound | Target (protein) | Effect |
|---|---|---|
| Trigonelline hydrochloride (1-methylpyridin-1-ium-3-carboxylic acid; chloride) (Antagonist) | NFE2L2 (Nuclear Factor, Erythroid 2 Like 2) | promotes follicle maturation (FIG. 4) |
| 3PO (3-pyridinyl)-1-(4-pyridinyl)-2-propen-1-one) (antagonist, Inhibitor). | PFKFB3 6-phosphfructo-2-kinase. | promotes follicle maturation (FIG. 5) |
| Ketotifen (4,9-dihydro-4-(1-methyl-4-piper-idylidende)-10H-benzo(4,5)cyclohepta(1,2,b)thiophen-10-one) (antagonist) | PDE8B (Phosphodiesterase 8B) | inhibits follicle maturation (FIG. 7) |
| Dyphylline (7-(2,3-dihydroxypropyl)-1,3-dimethylpurine-2,6-dione) (Antagonist) | PDE3B (Phosphodiesterase 3B) | Promotes follicle maturation (FIG. 9) |
| N-Carbamyl-L-glutamic acid ((2S)-2-(carbamoylamino)pentanedioic acid) (Antagonist) | CPS1 (Carbamoyl-Phosphate Synthase 1) | promotesfollicle maturation (FIG. 8) |
| Metformin (N,N-Dimethylimiddicarbonimiddiamid) | PRKAA1 (Protein Kinase AMP-Activated Catalytic Subunit Alpha 1) | promotes follicle maturation (FIG. 6) (AICAR, Metformin is ongoing) |
| PDGF-AA (peptide, expressed in E coli) (Agonist) | PDGFRA Platelet-derived growth factor receptor α | promotes follicle maturation (ongoing) |
| PF-562271 (N-methyl-N-[3-[[[2-[(2-oxo-1,3-dihydroindol-5-yl)amino]-5-(trifluoromethyl)pyrimidin-4-yl]amino]methyl]pyridin-2-yl]methanesulfonamide)(Antagonist) CT-707 (N/A) (antagonist) | PTK2B (Protein Tyrosine Kinase 2 Beta) | promotes follicle maturation (Ongoing) |
| BAY 1217389 (methyl 2,6-dimethyl-5-nitro-4-[2-(trifluoromethyl)phenyl]-1,4-dihydropyridine-3-carboxylate) (Antagonist) | TTK (Dual Specificity Protein Kinase) | promotes follicle maturation (Ongoing) |
| BI 836845 (ligand-neutralizing antibody) (= Xentuzumab)(antagonist) | IGF2 (Insulin Like Growth Factor 2) | promotes follicle maturation (ongoing) |
| SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate) | PIK3CB (Phosphatidylinositol-4,5-Bisphosphate 3-Kinase Catalytic Subunit Beta) | promotes follicle maturation (ongoing) |

TABLE 1-continued

| Compound | Target (protein) | Effect |
|---|---|---|
| Lavendustin (5-amino-((N-2,5-dihydroxybenzyl)-N'-2-hydroxybenzyl)aminosalicylic acid) | STIP1 (Stress Induced Phosphoprotein 1) | promotes follicle maturation (ongoing) |
| Picropodophyllin ((5R,5aR,8aS,9R)-5-hydroxy-9-(3,4,5-trimethoxyphenyl)-5a, 6,8a,9-tetrahydro-5H-[2]benzofuro[5,6-f][1,3]benzodioxol-8-one) (Antagonist). | IGF1R (Insulin Like Growth Factor 1 Receptor) | promotes follicle maturation (ongoing) |
| Linsitinib (3-[8-amino-1-(2-phenylquinolin-7-yl)imidazo[1,5-a]pyrazin-3-yl]-1-methylcyclobutan-1-ol) (Antagonist). | | |
| Cixutumumab (= IMC-A12) (a human IgG1 monoclonal antibody to the insulin-like growth factor I receptor) (Antagonist). | | |
| Ganitumab (Dasatinib) (N-(2-chloro-6-methylphenyl)-2-[[6-[4-(2-hydroxyethyl)piperazin-1-yl]-2-methylpyrimidin-4-yl]amino]-1,3-thiazole-5-carboxamide) (antagonist) | | |
| AVE1642 (Neratinib) ((E)-N-[4-[3-chloro-4-(pyridin-2-ylmethoxy)anilino]-3-cyano-7-ethoxyquinolin-6-yl]-4-(dimethylamino)but-2-enamide) (Antagonist) | | |
| XL228 (4-N-(5-cyclopropyl-1H-pyrazol-3-yl)-6-(4-methylpiperazin-1-yl)-2-N-[(3-propan-2-yl-1,2-oxazol-5-yl)methyl]pyrimidine-2,4-diamine) (Antagonist) | | |
| BIIB022 (4-[4-[[4-chloro-3-(trifluoromethyl)phenyl]carbamoylamino]phenoxy]-N-methyl-pyridine-2-carboxamide(Antagonist)) | | |
| Dalotuzumab (4-amino-N-(1-azabicyclo[3.3.1]nonan-4-yl)-5-chloro-2-methoxybenzamide)(formerly MK-0646)(Antagonist) | | |
| MM-141 ((antibody) (antagonist)) | | |
| PX-866 (acetic acid (1S,4E,10R,11R,13S,14R)-[4-diallylaminomethylene-6-hydroxy-1-methoxymethyl-10,13-dimethyl-3,7,17-trioxo-1,3,4,7,10,11,12,13,14,15,16,17-dodecahydro-2-oxa-cyclopenta[a]phenanthren-11-yl ester) | PIK3CB (Phosphatidylinositol-4,5-Bisphosphate 3-Kinase Catalytic Subunit Beta) | promotes follicle maturation (ongoing) |
| Dactolisib (-methyl-2-(4-(3-methyl-2-oxo-8-(quinolin-3-yl)-2,3-dihydro-1H-imidazo[4,5-c]quinolin-1-yl)phenyl)propanenitrile) | | |
| Pictilisib (2-(1H-indazol-4-yl)-6-(4-methanesulfonylpiperazin-1-ylmethyl)-4-morpholin-4-ylthieno(3,2-d)pyrimidine) | | |
| Buparlisib (5-(2,6-dimorpholinopyrimidin-4-yl)-4-(trifluoromethyl)pyridin-2-amine) | | |
| XI147 (Pilaralisib (2-amino-N-[3-({3-[(2-chloro-5-methoxyphenyl)amino]quinoxalin-2-yl}sulfamoyl)phenyl]-2-m)) | | |
| SAR260301 (S)-2-(2-(2-Methylindolin-1-yl)-2-oxoethyl)-6-morpholinopyrimidin-4(3H)-one) | | |
| Medorinone (5-methyl-1H-1,6-naphthyridin-2-one) (antagonist) | PDE3B (Phosphodiesterase 3B) | promotes follicle maturation (ongoing) |
| Cilostazol (6-[4-(1-cyclohexyltetrazol-5-yl)butoxy]-3,4-dihydro-1H-quinolin-2-one) (Sigma-Aldrich) (Antagonist) | | |
| Dipyridamole (2-[[2-[bis(2-hydroxyethyl)amino]-4,8-di(piperidin-1-yl)pyrimido[5,4-d]pyrimidin-6-yl]-(2-hydroxyethyl)amino]ethanol) (Antagonist) | | |
| Amrinone (3-amino-5-pyridin-4-yl-1H-pyridin-2-one) (Antagonist) | | |
| Tolbutamide (1-butyl-3-(4-methylphenyl)sulfonylurea) (Antagonist) | | |

TABLE 1-continued

| Compound | Target (protein) | Effect |
|---|---|---|
| Theophylline (1,3-dimethyl-7H-purine-2,6-dione) (Antagonist) | | |
| Pentoxifylline (3,7-dimethyl-1-(5-oxohexyl)purine-2,6-dione) (Antagonist) | | |
| Serdemetan (1-N-[2-(1H-indol-3-yl)ethyl]-4-N-pyridin-4-ylbenzene-1,4-diamine) (Antagonist) | MDM2 (Mouse Double Minute 2, Human Homolog Of; P53-Binding Protein) | promotes follicle maturation (ongoing) |
| CGM097 ((1S)-1-(4-chlorophenyl)-6-methoxy-2-[4-[methyl-[[4-(4-methyl-3-oxopiperazin-1-yl)cyclohexyl]methyl]amino]phenyl]-7-propan-2-yloxy-1,4-dihydroisoquinolin-3-one) (Antagonist) | | |
| DS-3032b (L-Erythro-hexonamide, 2,6-anhydro-5-((((3'R,4'S,5'R)-6''-chloro-4'-(2-chloro-3-fluoro-4-pyridinyl)-1'',2''-dihydro-4,4-dimethyl-2''-oxodispiro(cyclohexane-1,2'-pyrrolidine-3',3''-(3H)indol)-5'-yl)carbonyl)amino)-3,4,5-trideoxy-, 4-methylbenzenesulfon) (Antagonist) | | |
| MK-8242 (4-amino-1-[(2R,3S,4S,5R)-3,4-dihydroxy-5-(hydroxymethyl)oxolan-2-yl]pyrimidin-2-one) (Antagonist) | | |
| HDM201 ((6S)-5-(5-chloro-1,2-dihydro-1-methyl-2-oxo-3-pyridinyl)-6-(4-chlorophenyl)-2-(2,4-dimethoxy-5-pyrimidinyl)-5,6-dihydro-1-(1-methylethyl)-Pyrrolo[3,4-d]imidazol-4(1H)-one) (Antagonist) | | |
| Idasanutlin (4-{[(3S,4R,5S)-3-(3-Chloro-2-fluorophenyl)-4-(4-chloro-2-fluorophenyl)-4-cyano-5-(2,2-dimethylpropyl)-D-prolyl]amino}-3-methoxybenzoic acid) (antagonist) | | |
| RO6839921 (N/A) (antagonist) | | |
| RO5045337 ([(4S,5R)-2-(4-tert-butyl-2-ethoxyphenyl)-4,5-bis(4-chlorophenyl)-4,5-dimethylimidazol-1-yl]-[4-(3-methylsulfonylpropyl)piperazin-1-yl]methanone) (Antagonist) | | |
| AMG-232 (2-[(3R,5R,6S)-5-(3-chlorophenyl)-6-(4-chlorophenyl)-3-methyl-1-[(2S)-3-methyl-1-propan-2-ylsulfonylbutan-2-yl]-2-oxopiperidin-3-yl]acetic acid)(Antagonist) | | |
| APG-115 (Antagonist) | | |
| BMS-599626 ([(3S)-morpholin-3-yl]methyl N-[4-[[1-[(3-fluorophenyl)methyl]indazol-5-yl]amino]-5-methylpyrrolo[2,1-f][1,2,4]triazin-6-yl]carbamate) (antagonist) | ERBB4 (Erb-B2 Receptor Tyrosine Kinase 4) | promotes follicle maturation (ongoing) |
| Afatinib ((E)-N-[4-(3-chloro-4-fluoroanilino)-7-[(3S)-oxolan-3-yl]oxyquinazolin-6-yl]-4-(dimethylamino)but-2-enamide)(antanoist) | | |
| Osimertinib (N-[2-[2-(dimethylamino)ethyl-methylamino]-4-methoxy-5-[[4-(1-methylindol-3-yl)pyrimidin-2-yl]amino]phenyl]prop-2-enamide)(antagonist) | | |
| Poziotinib (1-[4-[4-(3,4-dichloro-2-fluoroanilino)-7-methoxyquinazolin-6-yl]oxypiperidin-1-yl]prop-2-en-1-one)(antagonist) | | |
| Pirotinib (4-methyl-N-[3-(4-methylimidazol-1-yl)-5-(trifluoromethyl)phenyl]-3-[(4-pyridin-3-ylpyrimidin-2-yl)amino]benzamide) | | |
| Pelitinib ((E)-N-[4-(3-chloro-4-fluoroanilino)-3-cyano-7-ethoxyquinolin-6-yl]-4-(dimethylamino)but-2-enamide)(antagonist) | | |

TABLE 2

| Compound | Target (protein) | Effect |
| --- | --- | --- |
| Trigonelline hydrochloride (1-methylpyridin-1-ium-3-carboxylic acid; chloride) (Antagonist) | NFE2L2 (Nuclear Factor, Erythroid 2 Like 2) | promotes follicle maturation (FIG. 4) |
| 3PO (3-pyridinyl)-1-(4-pyridinyl)-2-propen-1-one) (antagonist, Inhibitor). | PFKFB3 6-phosphfructo-2-kinase. | promotes follicle maturation (FIG. 5) |
| Ketotifen (4,9-dihydro-4-(1-methyl-4-piper-idylidende)-10H-benzo(4,5)cyclohepta(1,2,b)thiophen-10-one) (antagonist) | PDE8B (Phosphodiesterase 8B) | inhibits follicle maturation (FIG. 7) |
| Dyphylline (7-(2,3-dihydroxypropyl)-1,3-dimethylpurine-2,6-dione) (Antagonist) | PDE3B (Phosphodiesterase 3B) | Promotes follicle maturation (FIG. 9) |
| N-Carbamyl-L-glutamic acid ((2S)-2-(carbamoylamino)pentanedioic acid) (Antagonist) | CPS1 (Carbamoyl-Phosphate Synthase 1) | promotesfollicle maturation (FIG. 8) |
| Metformin (N,N-Dimethylimiddicarbonimiddiamid) | PRKAA1 (Protein Kinase AMP-Activated Catalytic Subunit Alpha 1) | promotes follicle maturation (FIG. 6) (AICAR, Metformin is ongoing) |
| PDGF-AA (peptide, expressed in *E coli*) (Agonist) | PDGFRA Platelet-derived growth factor receptor α | promotes follicle maturation (ongoing) |
| PF-562271 (N-methyl-N-[3-[[[2-[(2-oxo-1,3-dihydroindol-5-yl)amino]-5-(trifluoromethyl)pyrimidin-4-yl]amino]methyl]pyridin-2-yl]methanesulfonamide)(Antagonist) CT-707 (N/A) (antagonist) | PTK2B (Protein Tyrosine Kinase 2 Beta) | promotes follicle maturation (Ongoing) |
| BAY 1217389 (methyl 2,6-dimethyl-5-nitro-4-[2-(trifluoromethyl)phenyl]-1,4-dihydropyridine-3-carboxylate) (Antagonist) | TTK (Dual Specificity Protein Kinase) | promotes follicle maturation (Ongoing) |
| Bl 836845 (ligand-neutralizing antibody) (= Xentuzumab)(antagonist) | IGF2 (Insulin Like Growth Factor 2) | promotes follicle maturation (ongoing) |
| SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate) | PIK3CB (Phosphatidylinositol-4,5-Bisphosphate 3-Kinase Catalytic Subunit Beta) | promotes follicle maturation (ongoing) |
| Lavendustin (5-amino-((N-2,5-dihydroxybenzyl)-N'-2-hydroxybenzyl)aminosalicylic acid) | STIP1 (Stress Induced Phosphoprotein 1) | promotes follicle maturation (ongoing) |
| Picropodophyllin ((5R,5aR,8aS,9R)-5-hydroxy-9-(3,4,5-trimethoxyphenyl)-5a,6,8a,9-tetrahydro-5H-[2]benzofuro[5,6-f][1,3]benzodioxol-8-one) (Antagonist). Linsitinib (3-[8-amino-1-(2-phenylquinolin-7-yl)imidazo[1,5-a]pyrazin-3-yl]-1-methylcyclobutan-1-ol) (Antagonist). Cixutumumab (= IMC-A12) (a human IgG1 monoclonal antibody to the insulin-like growth factor I receptor) (Antagonist). Ganitumab (Dasatinib) (N-(2-chloro-6-methylphenyl)-2-[[6-[4-(2-hydroxyethyl)piperazin-1-yl]-2-methylpyrimidin-4-yl]amino]-1,3-thiazole-5-carboxamide) (antagonist) AVE1642 (Neratinib) ((E)-N-[4-[3-chloro-4-(pyridin-2-ylmethoxy)anilino]-3-cyano-7-ethoxyquinolin-6-yl]-4-(dimethylamino)but-2-enamide) (Antagonist) | IGF1R (Insulin Like Growth Factor 1 Receptor) | promotes follicle maturation (ongoing) |

TABLE 2-continued

| Compound | Target (protein) | Effect |
| --- | --- | --- |
| XL228 (4-N-(5-cyclopropyl-1H-pyrazol-3-yl)-6-(4-methylpiperazin-1-yl)-2-N-[(3-propan-2-yl-1,2-oxazol-5-yl)methyl]pyrimidine-2,4-diamine) (Antagonist) | | |
| BIIB022 (4-[4-[[4-chloro-3-(trifluoromethyl)phenyl]carbamoylamino]phenoxy]-N-methyl-pyridine-2-carboxamide(Antagonist)) | | |
| Dalotuzumab (4-amino-N-(1-azabicyclo[3.3.1]nonan-4-yl)-5-chloro-2-methoxybenzamide)(formerly MK-0646)(Antagonist) | | |
| MM-141 ((antibody) (antagonist)) | | |
| PX-866 (acetic acid (1S,4E,10R,11 R,13S,14R)-[4-diallylaminomethylene-6-hydroxy-1-methoxymethyl-10,13-dimethyl-3,7,17-trioxo-1,3,4,7,10,11,12,13,14,15,16,17-dodecahydro-2-oxa-cyclopenta[a]phenanthren-11-yl ester) | PIK3CB (Phosphatidylinositol-4,5-Bisphosphate 3-Kinase Catalytic Subunit Beta) | promotes follicle maturation (ongoing) |
| Dactolisib (-methyl-2-(4-(3-methyl-2-oxo-8-(quinolin-3-yl)-2,3-dihydro-1H-imidazo[4,5-c]quinolin-1-yl)phenyl)propanenitrile) | | |
| Pictilisib (2-(1H-indazol-4-yl)-6-(4-methanesulfonylpiperazin-1-ylmethyl)-4-morpholin-4-ylthieno(3,2-d)pyrimidine) | | |
| Buparlisib (5-(2,6-dimorpholinopyrimidin-4-yl)-4-(trifluoromethyl)pyridin-2-amine) | | |
| Xl147 (Pilaralisib (2-amino-N-[3-({3-[(2-chloro-5-methoxyphenyl)amino]quinoxalin-2-yl}sulfamoyl)phenyl]-2-m)) | | |
| SAR260301 (S)-2-(2-(2-Methylindolin-1-yl)-2-oxoethyl)-6-morpholinopyrimidin-4(3H)-one) | | |
| Medorinone (5-methyl-1H-1,6-naphthyridin-2-one) (antagonist) | PDE3B (Phosphodiesterase 3B) | promotes follicle maturation (ongoing) |
| Cilostazol (6-[4-(1-cyclohexyltetrazol-5-yl)butoxy]-3,4-dihydro-1H-quinolin-2-one) (Sigma-Aldrich) (Antagonist) | | |
| Dipyridamole (2-[[2-[bis(2-hydroxyethyl)amino]-4,8-di(piperidin-1-yl)pyrimido[5,4-d]pyrimidin-6-yl]-(2-hydroxyethyl)amino]ethanol) (Antagonist) | | |
| Amrinone (3-amino-5-pyridin-4-yl-1H-pyridin-2-one) (Antagonist) | | |
| Tolbutamide (1-butyl-3-(4-methylphenyl)sulfonylurea) (Antagonist) | | |
| Theophylline (1,3-dimethyl-7H-purine-2,6-dione) (Antagonist) | | |
| Pentoxifylline (3,7-dimethyl-1-(5-oxohexyl)purine-2,6-dione) (Antagonist) | | |
| Serdemetan (1-N-[2-(1H-indol-3-yl)ethyl]-4-N-pyridin-4-ylbenzene-1,4-diamine) (Antagonist) | MDM2 (Mouse Double Minute 2, Human Homolog Of; P53-Binding Protein) | promotes follicle maturation (ongoing) |
| CGM097 ((1S)-1-(4-chlorophenyl)-6-methoxy-2-[4-[methyl-[[4-(4-methyl-3-oxopiperazin-1-yl)cyclohexyl]methyl]amino]phenyl]-7-propan-2-yloxy-1,4-dihydroisoquinolin-3-one) (Antagonist) | | |
| DS-3032b (L-Erythro-hexonamide, 2,6-anhydro-5-((((3'R,4'S,5'R)-6''-chloro-4'-(2-chloro-3-fluoro-4-pyridinyl)-1'',2''-dihydro-4,4-dimethyl-2''-oxodispiro(cyclohexane-1,2'-pyrrolidine-3',3''-(3H)indol)-5'-yl)carbonyl)amino)-3,4,5-trideoxy-, 4-methylbenzenesulfon) (Antagonist) | | |

TABLE 2-continued

| Compound | Target (protein) | Effect |
|---|---|---|
| MK-8242 (4-amino-1-[(2R,3S,4S,5R)-3,4-dihydroxy-5-(hydroxymethyl)oxolan-2-yl]pyrimidin-2-one) (Antagonist) | | |
| HDM201 ((6S)-5-(5-chloro-1,2-dihydro-1-methyl-2-oxo-3-pyridinyl)-6-(4-chlorophenyl)-2-(2,4-dimethoxy-5-pyrimidinyl)-5,6-dihydro-1-(1-methylethyl)-Pyrrolo[3,4-d]imidazol-4(1H)-one) (Antagonist) | | |
| Idasanutlin (4-{[(3S,4R,5S)-3-(3-Chloro-2-fluorophenyl)-4-(4-chloro-2-fluorophenyl)-4-cyano-5-(2,2-dimethylpropyl)-D-prolyl]amino}-3-methoxybenzoic acid) (antagonist) | | |
| RO6839921 (N/A) (antagonist) | | |
| RO5045337 ([(4S,5R)-2-(4-tert-butyl-2-ethoxyphenyl)-4,5-bis(4-chlorophenyl)-4,5-dimethylimidazol-1-yl]-[4-(3-methylsulfonylpropyl)piperazin-1-yl]methanone) (Antagonist) | | |
| AMG-232 (2-[(3R,5R,6S)-5-(3-chlorophenyl)-6-(4-chlorophenyl)-3-methyl-1-[(2S)-3-methyl-1-propan-2-ylsulfonylbutan-2-yl]-2-oxopiperidin-3-yl]acetic acid)(Antagonist) | | |
| APG-115 (Antagonist) | | |
| BMS-599626 ([(3S)-morpholin-3-yl]methyl N-[4-[[1-[(3-fluorophenyl)methyl]indazol-5-yl]amino]-5-methylpyrrolo[2,1-f][1,2,4]triazin-6-yl]carbamate) (antagonist) | ERBB4 (Erb-B2 Receptor Tyrosine Kinase 4) | promotes follicle maturation (ongoing) |
| Afatinib ((E)-N-[4-(3-chloro-4-fluoroanilino)-7-[(3S)-oxolan-3-yl]oxyquinazolin-6-yl]-4-(dimethylamino)but-2-enamide)(antanoist) | | |
| Osimertinib (N-[2-[2-(dimethylamino)ethyl-methylamino]-4-methoxy-5-[[4-(1-methylindol-3-yl)pyrimidin-2-yl]amino]phenyl]prop-2-enamide)(antagonist) | | |
| Poziotinib (1-[4-[4-(3,4-dichloro-2-fluoroanilino)-7-methoxyquinazolin-6-yl]oxypiperidin-1-yl]prop-2-en-1-one)(antagonist) | | |
| Pirotinib (4-methyl-N-[3-(4-methylimidazol-1-yl)-5-(trifluoromethyl)phenyl]-3-[(4-pyridin-3-ylpyrimidin-2-yl)amino]benzamide) | | |
| Pelitinib ((E)-N-[4-(3-chloro-4-fluoroanilino)-3-cyano-7-ethoxyquinolin-6-yl]-4-(dimethylamino)but-2-enamide)(antagonist) | | |

Example 2

Materials and Methods

Ovaries Cultures

Ovaries obtained from mice were washed twice with culture medium. Antagonists or agonists to be tested were dissolved in suitable solvents and added to the medium. As a control medium comprising solvent without the antagonist or agonist was used. One of the ovaries was cultured in a control medium and another was cultured with the antagonist or agonist. The tested antagonists or agonists and their concentrations are outlined in table 2.

Ovaries were incubated with antagonist at 37° C. and 5% $CO_2$ for 24 and 96 hours, respectively (see table 3).

TABLE 3

| Antagonist or agonist | Substrate | Concentration of antagonist/agonist | Incubation time |
|---|---|---|---|
| AICAR | Activator of AMP-activated protein kinase (AMPK) | 1 mM | 96 hours |
| Dorsomorphin | AMPK inhibitor | 5 μM | 96 hours |
| 3PO | 6-phosphfructo-2-kinase inhibitor | 30 μM | 96 hours |
| PDGF-AA (Sigma) | Platelet-derived growth factor receptor α (PDGFRA) agonist | 10 ng/mL | 96 hours |
| PDE8B | Ketotifen | 85 nM | 96 hours |
| CPS1 | N-Carbamyl-L-glutamic acid | 10 mM | 96 hours |

TABLE 3-continued

| Antagonist or agonist | Substrate | Concentration of antagonist/agonist | Incubation time |
|---|---|---|---|
| NFE2L2 | Trigonellin hydrochloride | 1.0 µM | 96 hours |

Cultures ovaries were fixed, embedded in paraffin and sliced microscopy. The sectioned ovaries were stained with hematoxylin and eosin (H&E) to visualize the morphology of the ovary by microscopy.

Histological Analysis and Follicle Classification

The number of primordial, primary and secondary follicles was determined, and it was determined whether the antagonist or agonist was capable of regulating folliculogenesis.

3PO—a PFKFB3 Inhibitor That

Figure 3:
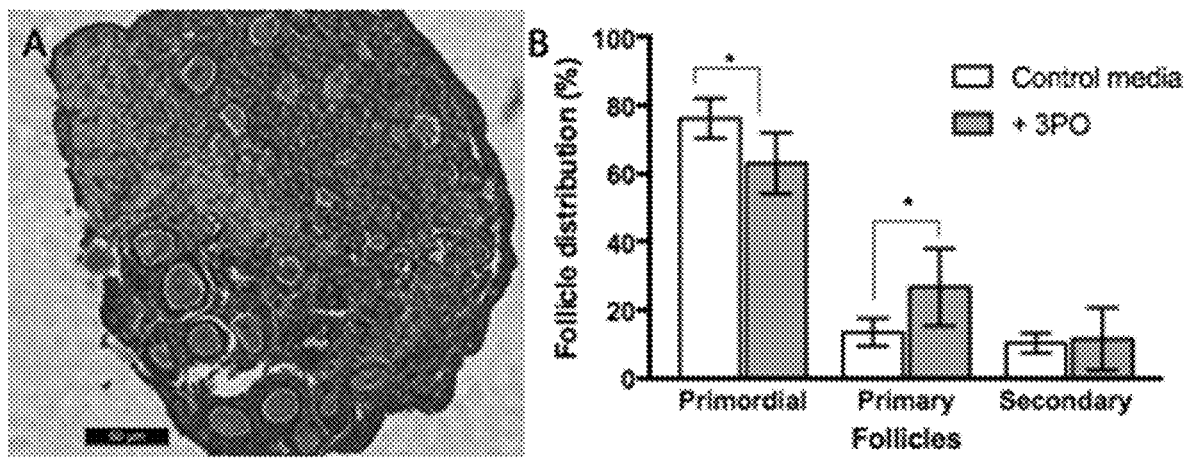
FIG. 3: Ovaries treated with 3PO. (A) H&E staining of paraffin section of a whole ovary cultured with 30 μM 3PO for four days. (B) Follicle distribution of ovaries incubated with 3PO or in control media. Significant differences (P<0.05) are marked with an asterisks.

The PFKFB3 inhibitor 3PO (30 µM) was added to the medium and ovaries were cultured therein for four days. For statistical analysis only the healthy follicles were counted. Ovaries cultured with 3PO contained 63.11±8.83% primordial follicles, whereas control ovaries contained 76.15±5.81%, resulting in a significant decrease in primordial follicles (P=0.01282) when treated with 3PO. The control ovaries held 13.50±4.02% primary follicles and ovaries treated with 3PO held 26.60±11.24% primary follicles. The difference between the two groups of primary follicles was significantly different (P=0.022794). Ovaries treated with 3PO contained 11.58±9.07% secondary follicles and control ovaries contained 10.35±2.89% secondary follicles. The follicle distribution is illustrated in FIG. 3B.

AICAR—Activator of AMPK

In order to investigate the effects of AICAR on primordial-to-primary follicle transition in vitro ovaries were cultured in medium containing 1 mM AICAR (FIG. 4A) or ddH$_2$O (appendix 14) for four days. It was observed that ovaries cultured in medium with AICAR contained 86.02±5.84% primordial follicles whereas untreated ovaries only contained 68.25±5.965% primordial follicles, thus does incubation with AICAR results in a significantly difference in the number of primordial follicles (P=0.00022). There was also significant difference in the number of primary follicles in ovaries threated with or without AICAR (P=0.00428), since AICAR treated ovaries only held 10.82±4.98% primary follicles versus untreated ovaries which contained 20.90±4.52% primary follicles. Furthermore, it was observed that only 3.0±3.09% of all follicles were characterized secondary when treated with AICAR, whereas 10.73±2.92% were characterized secondary in the control medium, a difference which is significant (P=0.00122). The follicle distribution is presented in FIG. 4B.

Dorsomorphin

To verify if inhibition of AMPK could be involved in the primordial-to-primary follicle transition, 5 µM dorsomorphin was added to the medium and incubated for four days (FIG. 15A and appendix 16). The control medium was contaminated, therefore the results from ovaries treated with dorsomorphin are compared to the results illustrated in FIG. 7. The ovaries treated with dorsomorphin contained 71.32±5.50% primordial follicles whereas control ovaries contained 76.15±4.02% primordial follicles, however, the difference between the two groups is not significant (P=0.1694). The number of primary follicles is neither significant (P=0.74224), since the dorsomorphin treated ovaries contain 12.78±2.23% primary follicles and untreated ovaries held 13.495±4.02% primary follicles. However, there was a significant difference between the number of secondary follicles (P=0.00938), since the dorsomorphin treated ovaries contained 15.87±3.06% secondary follicles and the untreated ovaries held 10.35±2.89%. The follicle distribution is illustrated in FIG. 5B.

Ketotifen—an Inhibitor of PDE8B

Figure 6:
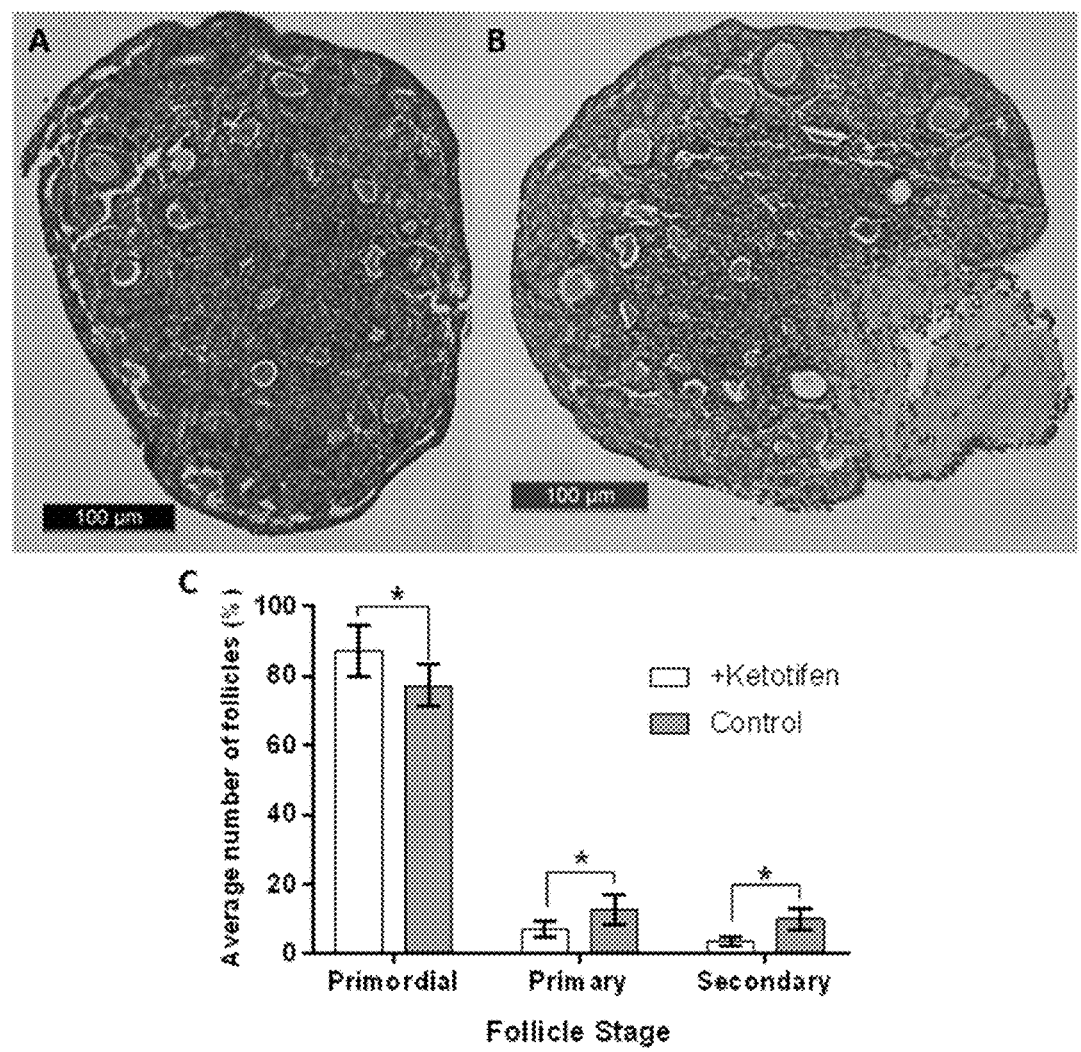
FIG. 6: Effect of the PDE8B inhibitor Ketotifen on Follicle Distribution. (A) H&E stained paraffin sections of ovaries cultured for 96 hours with 85 nM Ketotifen or (B) without (control). (C) Follicle distribution of ovaries incubated with Ketotifen or in control media. Three sections were counted for each treatment. The average number of follicles (%) is represented (±standard errors of the mean). Significant differences (P<0.05) are marked with an asterisk.

The transcriptome study discussed in Example 1 shows that PDE8B was up-regulated and therefore, had a higher expression in primary follicles than in primordial follicles. PDE8B is the gene encoding the protein phosphodiesterase 8B. Ovaries were cultured with 85 nM Ketotifen for 96 hours. Afterwards they were dehydrated, paraffin embedded and stained with H&E in sections of 5 µm. Our analysis showed a significant difference (P<0.05) between the treated group (Ketotifen) and the control group (FIG. 6). When ovaries were treated with the PDE8B inhibitor there were approximately 9% more primordial follicles (P=0.029), 44% less primary follicles and 65% less secondary follicles (P=0.019).

N-Carbamoyl-L-Glutamic Acid—Upregulates the Activity of CPS1

Figure 7:
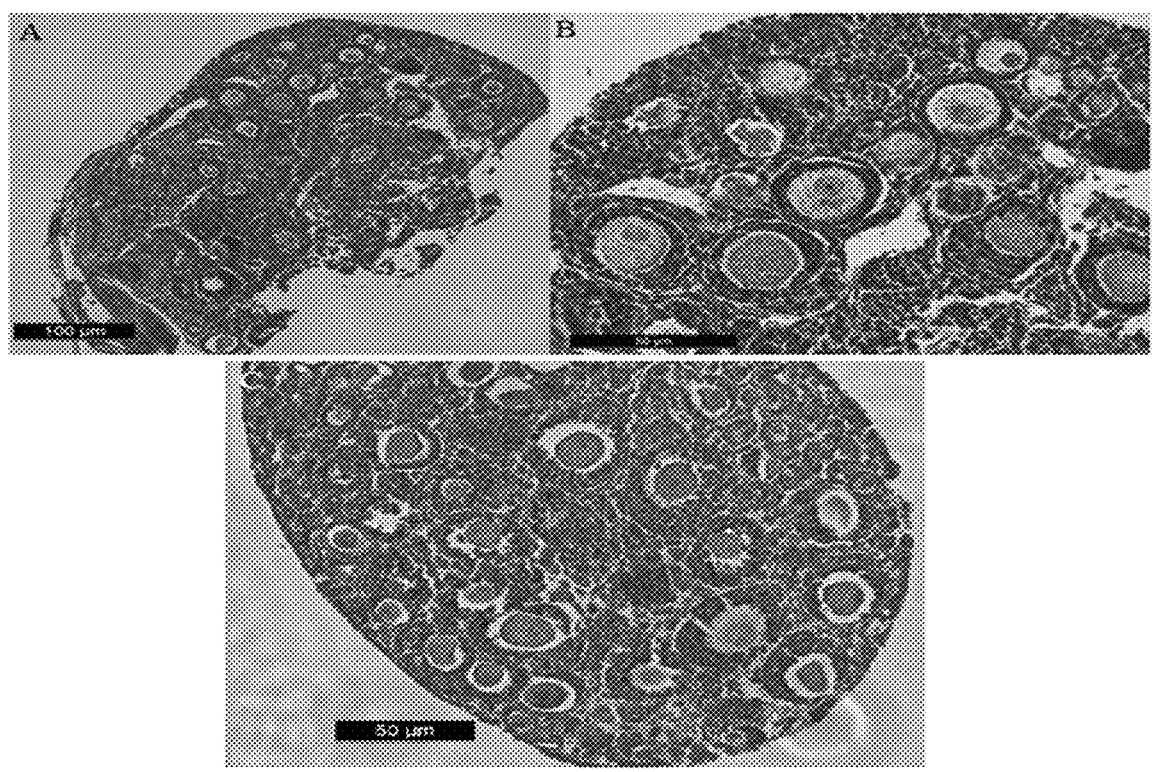
FIG. 7. The effect of the CPS1 protector NCG on Follicle Distribution. (A) and (B) Ovaries were treated with 10 mM NCG and cultured for 96 hours. Sections were stained with H&E. (A) 200× magnification, (B) 400× magnification. (C) Ovary treated with control medium with DMSO.

The transcriptome study disclosed in Example 1 shows that the carbamoyl-phosphate synthase 1 gene (CPS1) is down regulated. The gene CPS1 had a higher expression in primordial follicles compared to primary follicles. N-Carbamoyl-L-glutamic acid (NCG) was added to the medium in a concentration of 10 mM. FIG. 7 demonstrates that the follicles were very well shaped and oocytes were intact when treated with NCG compared to other treatments (FIG. 7).

Trigonellin Hydrochloride—an Inhibitor of Nrf2

Figure 11:
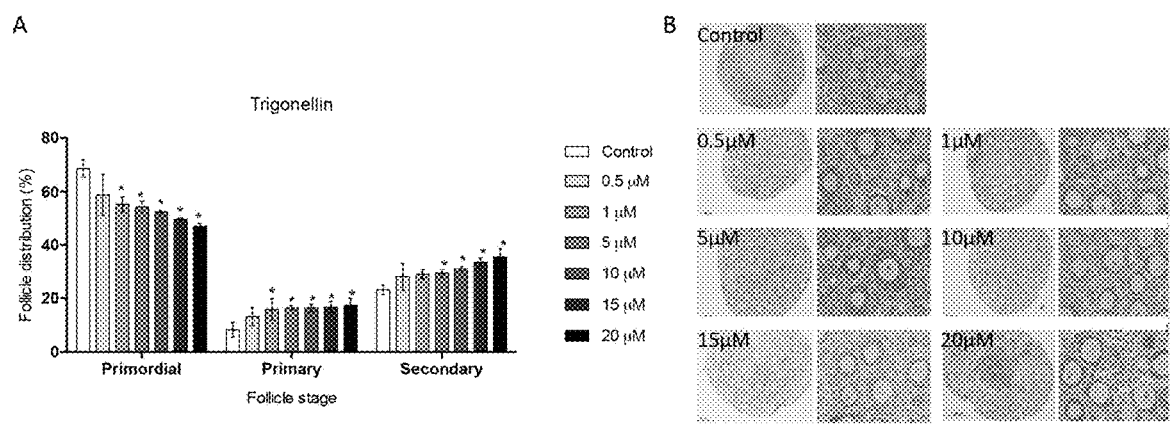

Nuclear factor, erythroid 2-like 2 (NFE2L2 or Nrf2) gene is indicated to be up-regulated in primary follicles according to the transcriptome study disclosed in Example 1. Ovaries were cultured for 96 hours in medium supplemented with 1.0 µM Trigonellin hydrochloride. FIG. 11 shows ovaries treated with Trigonellin hydrochloride medium and control medium after H&E staining. The statistical analysis showed that there was a significant decrease (~20%) in the average numbers of primordial follicles (P=9.9·10$^{-4}$) and a significant increase (~74%) compared to the control (P=9.5·10$^{-4}$) (see FIG. 9).

Example 3

Methods

Animals

C57BL/6j×CBA F1 hybrid mice (Janvier Labs, France) were housed and bred in the animal facilities at Department of Biomedicine, Aarhus University. Animals were housed in a 12:12 h controlled light-dark environment and were provided with food and water ad libitum. 7-day-old female pups were used for the study.

Isolation of Ovaries and Organ Culture

Pups were sacrificed and ovaries were excised. Using a stereomicroscope MZ75 (Leica Microsystems, Germany), excess tissue was removed. During the dissection, ovaries were kept at 37° C. in culture medium: aMEM (Thermo Fisher) supplemented with 10% FBS (Thermo Fisher), 100 mIU/mL of FSH (Sigma-Aldrich), 100 IU/mL penicillin (Thermo Fisher), 100 µg/mL streptomycin (Thermo Fisher) and 1% Insulin-Transferrin-Selenium (Thermo Fisher). Isolated ovaries were transferred into well inserts (PET membrane ThinCert, 0.4 µm-pore size; Greiner bio-one) in 24-well plates (Tissue culture treated, cell culture plates; Costar). 200-300 µL of culture medium was added to the well below the insert and up to two ovaries were placed on the membrane of each insert. The culture medium was supplemented with different concentrations of the tested compounds; bpV(HOpic) (Sigma-Aldrich), Temsirolimus (Sigma-Aldrich), Ketotifen (Sigma-Aldrich), 3PO (Sigma-Aldrich), Dorsomorphin (Sigma-Aldrich), AICAR (Sigma-Aldrich), NCG (Sigma-Aldrich), and Dyphylline (Cayman Chemical). Up to six wells in the 24-well plate were used for inserts. Sterile $dH_2O$ was added to the rest of the wells to ensure humidity and reduce evaporation. The ovaries were cultured at 37° C., 5% $CO_2$ for four days. 150 μL of medium was replaced every other day with fresh culture medium.

Histological Analysis and Follicle Counting

Ovaries kept in organ culture for four days were fixed for 24 hours in 4% paraformaldehyde solution at 4° C. After fixation, ovaries were dehydrated in ethanol series using 70%, 96% and 99.9% ethanol. Xylene was used as clearing agent before the ovaries were infiltrated in paraffin wax. 5 μm-sections of samples in paraffin were cut using a microtome (Cut 6062, SLEE medical, Germany). Paraffin sections were mounted on glass slides, paraffin was melted at 60° C., and the samples were stained with hematoxylin and eosin (using standard protocols).

The samples were deparaffinized by incubating in xylene for 2×15 min. and subsequently rehydrated in series of ethanol; 3×2 min. in 99.9% ethanol, 2 min. in 96% ethanol, and 2 min. in 70% ethanol. The samples were then rinsed in $dH_2O$, stained in hematoxylin for 40 sec., rinsed in $dH_2O$ for 5 min., and stained in eosin for 46 sec. The samples were dehydrated in ethanol: 2×2 min. in 96% ethanol, 2×2 min in 99.9% ethanol, and finally cleared up in xylene for at least 30 min before mounting the samples using Eukitt mounting medium (Sigma-Aldrich) and cover glass.

The number of follicles at each developmental stage was counted using an inverted research microscope (DM14000B, Leica Microsystems, Germany). The follicles of every $3^{rd}$ to $4^{th}$ section of each ovary were counted and the distribution of follicles in the different stages in percentage was determined. Every treatment was repeated on at least three biological repeats. Only follicles with a visible oocyte nucleus was counted. Follicles were classified as either primordial, primary and secondary. Briefly, primordial follicles consist of an oocyte encapsulated by flattened, squamous granulosa cells. Primary follicles are oocytes encapsulated by one layer of cuboidal granulosa cells, and secondary follicles consist of oocytes encapsulated by more than one layer of cuboidal granulosa cells.

Statistical Analysis

The percentages of follicles in the different stages from each biological repeat were averaged. When comparing two groups, an unpaired t-test was performed. One-way ANOVA followed by determination of statistical significance using the Holm-Sidak method was performed when comparing more than two groups. Groups were considered significantly different if $P \leq 0.05$. Statistics were calculated with the help of GraphPad Prism (version 7.00 GraphPad Software, La Jolla, Calif., USA).

Results

Using mouse as our experimental model system, we have optimized a very robust and reliable in vitro system to test compounds for their ability to activate—or inhibit—oocytes from primordial follicels and subsequently, evaluate the distribution of primary and secondary follicles (FIG. 9A), We have excellent end-point testing to functionally address if the quality of the cells are maintained well enough for the oocyte to be fertilized. Once a compounds is selected for further testing, single follicels will be cultured in a 3D gel (FIG. 9B), and the resulting mature oocytes will be submitted to in vitro fertilization and transferred back in a female mouse, to evaluate its potential to form an embryo (FIG. 9B).

As control experiments, we targeted the PI3K/PTEN/Akt pathway, the PTEN inhibitor bpV(HOpic), a bisperoxovanadium inhibitor that has been shown to have an apparent effect on primordial follicle activation[13,18-20.] We further targeted the mTOR/Tsc pathway, by inhibition of mTORC1 using the Rapamycin analogue Temsirolimus (C56H87N016) with the aim to decrease follicle activation, as rapamycin appears to have an antagonizing effect on primordial follicle activation[21]. By using these two antagonists we established a system allows us to manipulate the rate of primordial-to-primary transition as well as decrease the rate of primordial-to-primary transition.

Control Compounds.

In order to establish the in vitro screening system, we tested our system using two known compounds that induce and inhibit primordial follicle activation, respectively. To target the PI3K/PTEN/Akt pathway, the PTEN inhibitor bpV(HOpic) was chosen. This inhibitor has been shown to have an apparent effect on primordial follicle activation[13, 18-20.] Our transcriptome analysis suggested that the PI3K/AKT/PTEN pathway is differentially expressed, which made PTEN a great control target. To target the mTOR/Tsc pathway, inhibition of mTORC1 was utilized with the Rapamycin analogue Temsirolimus with the aim to decrease follicle activation, as rapamycin appears to have an antagonizing effect on primordial follicle activation[21].

bpV(HOpic)

Biochemical and genetic manipulation studies in the mouse have identified the PI3K-AKT signaling pathway as a key mechanism involved in the maintenance of follicle growth and loss[13]. The pathway is reversed by the action of PTEN which causes dephosphorylation of PIP3 thus regulating the initiation of follicle growth and preventing premature exhaustion of the follicle pool.

Figure 10:
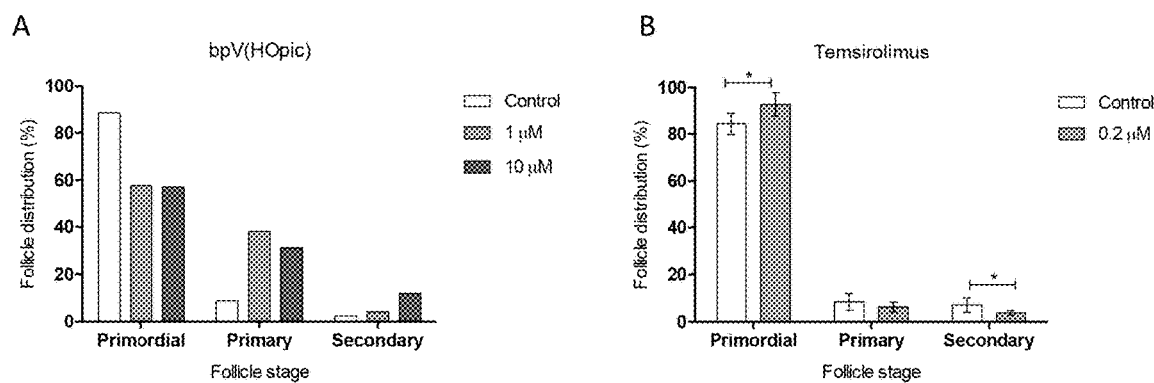
FIG. 10. (A) Effect of the PTEN Inhibitor bpV(HOpic) on Follicle distribution. The average number of follicles (%) are represented at three follicle stages (Bruun et al, unpublished). (A) Ovaries treated with the mTORC1 inhibitor Temsirolimus. Follicle distribution was evaluated and counted, and a t-test was performed to determine significant differences (P<0.05). Significant results are marked with an asterisks FIG. 11 (A) Percentage of follicles at different developmental stages in different concentration of Trigonellin before and after culture of ovaries. Values are given as mean±SE. a: Significant differences with non-cultured ovaries (P<0.05). b: Significant differences with control group (P<0.05). c: Significant differences with cultured ovaries in 0.5 µM Trigonellin (P<0.05). (Amoushashi and Lykke-Hartmann, unpublished) (B) Photomicrographs of whole mouse ovary sections using hematoxylin and eosin staining without culture (A) and after (B) 7 days culture, and with trigonellin treatments at (C) 0.5 µM, (D) 1 µM, (E) 5 µM, (F) 10 µM, (G) 15 µM and (H) 20 µM. Scale bars 100 or 50 µM, as indicated (Amoushashi and Lykke-Hartmann, unpublished).

The PTEN inhibitor bpV(HOpic) is a bisperoxovanadium inhibitor that affect on primordial follicle activation[13] by inhibiting the PI3K/PTEN/Akt pathway. Using bpV (HOpic), we proved that the in vitro system allows us to manipulate the increase the rate of primordial-to-primary transition (FIG. 10A)

Temsirolimus

The inhibition of mTORC1 using the Rapamycin analogue Temsirolimus (C56H87N016) inhibits the mTOR/Tsc pathway, and thereby decrease follicle activation, as rapamycin appears to have an antagonizing effect on primordial follicle activation[21]. By using Temsirolimus, we prove that the system allows us to manipulate a decrease the rate of primordial-to-primary transition (FIG. 10B).

NRF2

NRF2 is a transcription factor that upregulates the expression of a battery of genes to combat oxidative and electrophilic stress. Under unstressed conditions, NRF2 forms a complex leading to its degradation. Upon exposure to a variety of stressors, including ROS, toxicants, and carcinogens, NRF2 is released and translocates into the nucleus and binds to antioxidant response elements (AREs) on the promoter region of various genes. We used the NRF2 inhibitor Trigonellin in our ovary in vitro culture system. The medical value of Trigonellin is very high and already clinically approved for other conditions such as decreased blood glucose levels, and possess anti-carcinogenic, anti-migraine, hypocholesterolemic, and anti-diabetic activities. We carried out a titration range of trigonellin concentrations (FIG. 11A)

and monitored the morphological appearance (FIG. 11B). We found that most concentrations of Trigonellin caused a significant decrease of primordial follicles compared to control groups (FIG. 11A)

3PO

Figure 12:
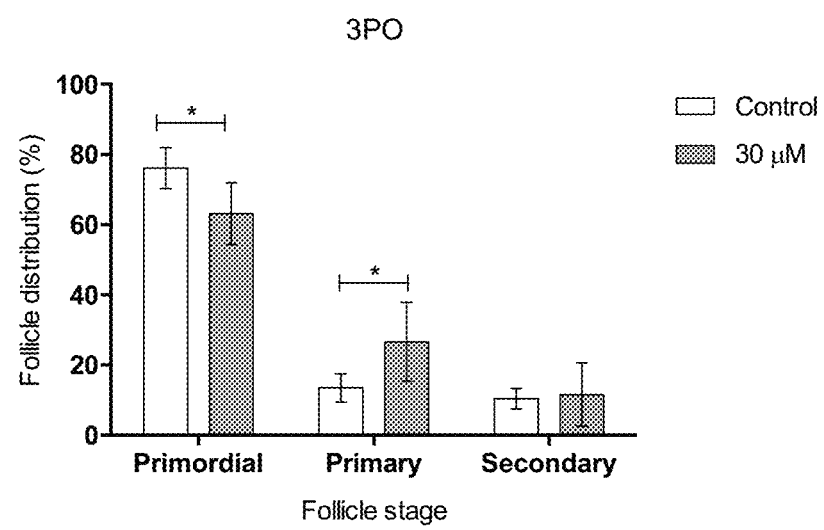
FIG. 12. Follicle distribution in ovaries treated with 3PO. The graph illustrates the follicle distribution on ovaries treated with or without 3PO. Significant differences (P<0.05) are marked with an asterisks

We further tested 3PO (Sigma-Aldrich) (antagonist, Inhibitor), small molecule antagonist 3-(3-pyridinyl)-1-(4-pyridinyl)-2-propen-1-one) that is a potent and selective inhibitor of PFKFB3 (6-Phosphofructo-2-kinase/fructose-2, 6-bisphosphatase), and found that ovaries cultured with 3PO contained 63.11±8.83% primordial follicles, whereas control ovaries contained 76.15±5.81%, resulting in a significant decrease in primordial follicles (p=0.01282) when treated with 3PO (FIG. 12).

AMPK

We tested AICAR (Sigma-Aldrich), an AMPK activator. Ovaries isolated from juvenile F1 mice were in vitro cultured for four days in control medium (0 mM AICAR) or medium containing different concentrations of AICAR: 0.1 mM, 0.2 mM, 0.4 mM, 0.5 mM, 1 mM to determine the optimal concentration for ovaries to be incubated with AICAR. AICAR is an activator of AMPK, and we hypothesized that activation of AMPK would maintain more primordial follicles in dormancy. However, growing follicles within the ovary tended to appear unhealthy and the oocytes were not able to maintain a round structure, however the follicle distribution were counted anyway.

Figure 13:
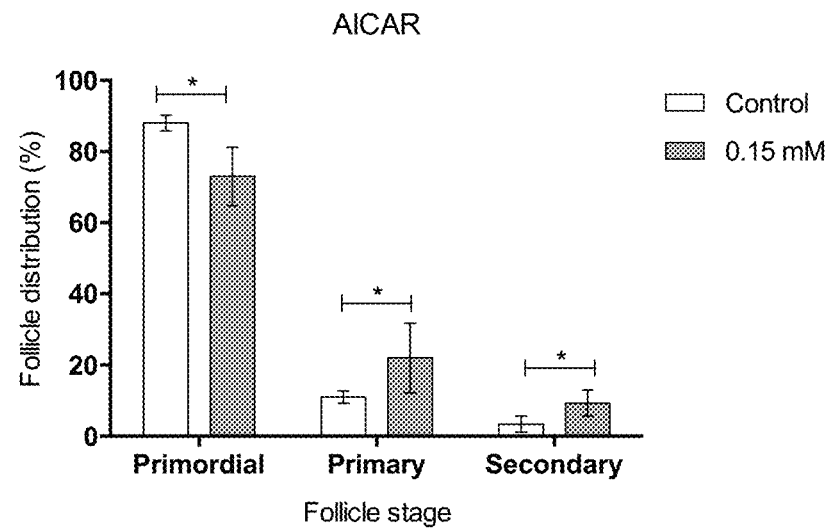
FIG. 13: ovary treated with AMPK activator AICAR. After 4-day of culture with 1 mM AICAR, the follicle distribution in ovaries treated with or without AICAR was evaluated. The asterisks indicate significant differences FIG. 14. Effect of the PDE8B inhibitor Ketotifen on Follicle Distribution. Ovaries cultured for 96 hours with 85 nM Ketotifen or without (control). Three sections were counted for each treatment. The average number of follicles (%) are represented (±standard errors of the mean).

In vitro ovaries were cultured in medium containing 1 mM AICAR, and found that incubation that ovaries cultured in medium with AICAR contained 86.02±5.84% primordial follicles whereas untreated ovaries only contained 68.25±5.965% primordial follicles, thus does incubation with AICAR results in a significantly difference in the number of primordial follicles (P=0.00022). There was also significant difference in the number of primary follicles in ovaries threated with or without AICAR (P=0.00428), since AICAR treated ovaries only held 10.82±4.98% primary follicles versus untreated ovaries which contained 20.90±4.52% primary follicles. Furthermore, it was observed that only 3.0±3.09% of all follicles were characterized secondary when treated with AICAR, whereas 10.73±2.92% were characterized secondary in the control medium, a difference which is significant (P=0.00122) (FIG. 13).

We also tried a lower concentration. Ovaries cultured with 0.5 mM AICAR contained 83.83±3.06% (n=1) meaning that 0.5 mM AICAR also were significantly able to inhibit the activation of primordial follicles (P=0.0079)(data not shown), however the concentration still seemed too harsh for the growing follicles.

We are now in progress of testing metformin, as an alternative an AMPK activator.

PDE8B

PDE8B is the gene encoding the protein phosphodiesterase 8B (PDE8B). PDE8B along with other phosphodiesterase genes have previously been shown to be present in the human ovary (Petersen et al. 2015; Guillemette et al. 2009). Phosphodiesterase are enzymes which degrade cyclic adenosine monophosphate (cAMP). cAMP is made as a result of G-protein couple receptor (GPCS) activation by adenylate cyclase. FSH and LH both bind GPCRs thereby leading to the formation of cAMP. cAMP is an important second messenger and studies indicated that it increased follicle growth and increased expression of the KL gene in granulosa cells when human ovarian chips were cultured with 8-bromo-cAMP (Zhang et al. 2004). It was thus theorized that inhibition of PDE8B would lead to increased follicle growth because of increased intracellular cAMP. Contrary to this hypothesis, Conti et al. (2002) describes how high levels of cAMP inside the oocyte may inhibit meiotic resumption of oocytes by holding phosphokinase A in an active state. They theorized that the high intra oocyte cAMP concentration may be produced by transport of cAMP from granulosa cells through gap-junctions. This was postulated because inhibition of PDE3A (PDE in oocytes) was found to prevent oocyte maturation whereas PDE4 (PDE in granulosa cells) inhibitors led to continuation of oocyte maturation in mouse ovaries (Conti et al. 2002). Guillemette et al. (2009) demonstrated that inhibition of PDE8 in cumulus cells increased cAMP in the cumulus-oocyte-complex, which resulted in delayed maturation of oocytes in bovine ovaries.

Figure 14:
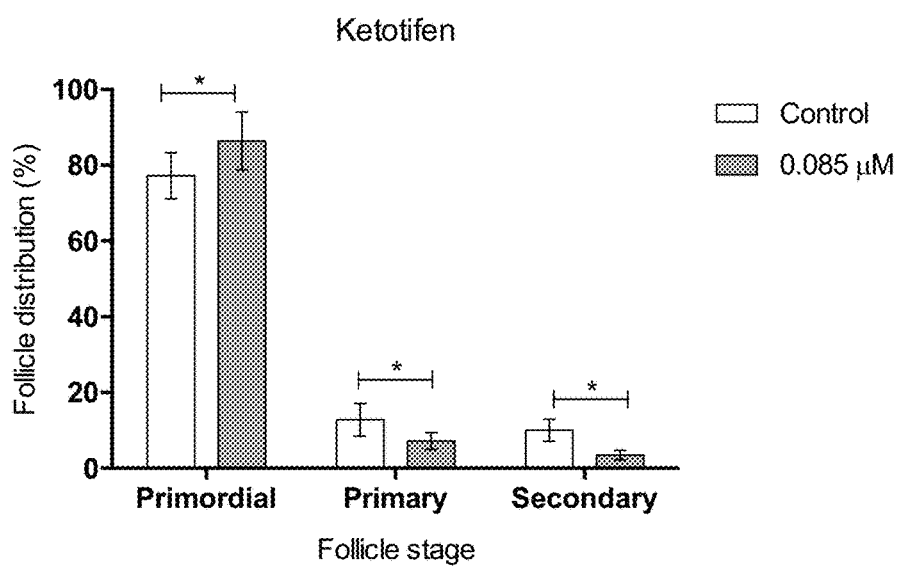

As a Target of PDE8B, we used Ketotifen. Ovaries were cultured for 96 hours with 85 nM Ketotifen. Afterwards they were dehydrated, paraffin embedded and stained with H&E in sections of 5 μm. Our analysis showed a significant difference (P<0.05) between the treated group (Ketotifen) and their control group (who received medium supplemented with ddH$_2$O) (FIG. 14). Ovaries treated with the PDE8B inhibitor there were approximately 9% more primordial follicles (P=0.029), 44% less primary follicles and 65% less secondary follicles (P=0.019) (FIG. 14)

CPS1

CPS1 is an enzyme important for the urea cycle which catalyzes the first reaction: the conversion of ammonium to carbamoyl phosphate. It has been suggested that accumulation of ammonium in the follicular fluid and altered gene expression profile was associated with reduced ovarian reserve and advanced maternal age Pacella-ince et al. (2014). Ammonium levels were used as a marker for CPS1 activity and their study indicated that women with reduced ovarian reserve and advanced maternal age had an increase in ammonium levels, thus a decrease in CPS1 activity (Pacella-ince et al. 2014). Based on this report (Pacella-ince et al. 2014), it would be interesting to test how protection against proteolytic cleavage and other degrading factors of CPS1 would impact our in vitro cultured ovaries.

Figure 15:
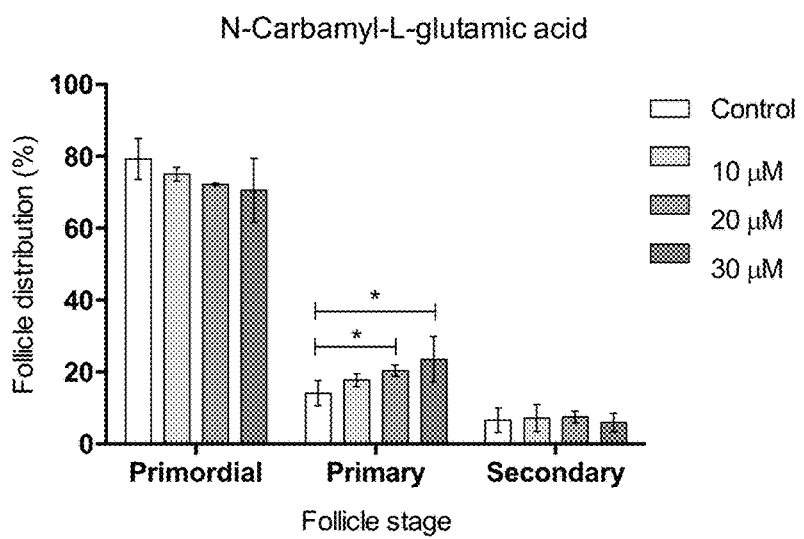
FIG. 15. The effect of the CPS1 protector NCG on Follicle Distribution. Ovaries were cultured with 10, 20 or 30 µM NCG and follicels distribution was evaluated after 96 hours of incubation FIG. 16. The effect of the Dyphylline on Follicle Distribution. Ovaries were cultured with 10 or 100 µM Dyphylline and follicels distribution was evaluated after 96 hours of incubation

N-Carbamoyl-L-glutamic acid (NCG) has been reported to protect human CPS1 against proteolytic cleavage (Diez-Fernandez et al. 2013). NCG was added to the medium supporting ovary culturing in a concentration of 10, 20 and 30 μM. This revealed that NCG has the potential to activate primordial follicle distribution (FIG. 15).

PDE3B

Figure 16:
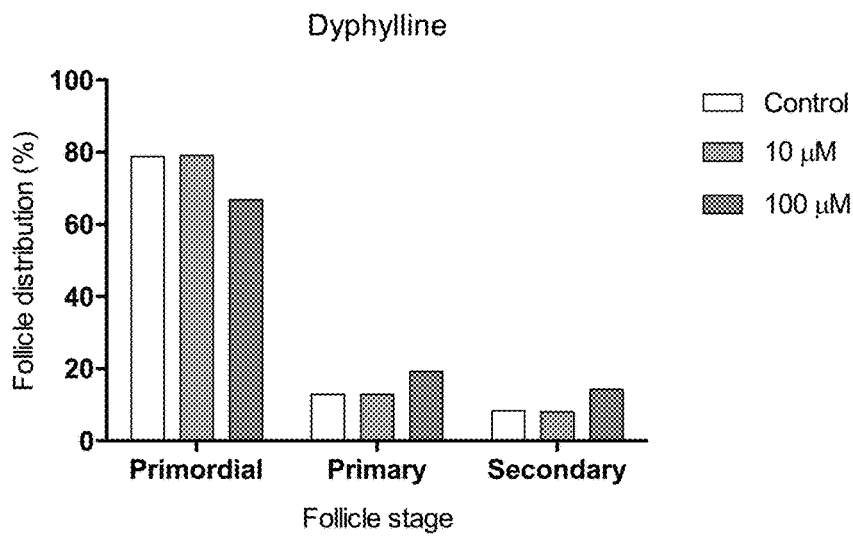

Phosphodiesterase-3 (PDE3) is a major cAMP-hydrolyzing PDE in oocytes[24]. We analysed the potential of PDE3B to manipulate follicle distribution by using Dyphylline. Dyphylline was added to the medium supporting ovary culturing in a concentration of 10 and 100 μM. This revealed that Dyphylline has the potential to activate primordial follicle distribution (FIG. 16), although the number analysed is still too small to perform statistic testings.

Discussion

The potential impact of the presented results on our understanding of human follicle dormancy, activation and integrity is discussed below.

NRF2

NFR2 is a regulator of potential toxic substances. As reported in Section 4.3.3, Nrf2 null mice treated with an ovarian toxin showed accelerated follicular development (Hu et al. 2006). The current study also indicates that Nrf2 is important for maintaining dormancy of follicles. A significant decrease in primordial follicle distribution and a significant increase in primordial follicle distribution was apparent in ovaries treated with Nrf2 inhibitor compared to the control. As Hu et al. (2006) hypothesized, an increase in follicular development might be due to reduced Foxo3a expression. Indeed, NFE2L2 null-mice showed significantly reduced Foxo3a (Hu et al. 2006). Investigations of the interplay between the mTORC1 pathway and Nrf2 activity would be an interesting subject.

PFKFB3

PFKFB3 is important for regulation of glycolysis in the cytoplasm but also for the control of cell cycle in the nucleus. PFKFB3 converts fructose-6-phosphat (F6P) into fructose-2,6-bisphosphate (F2,6BP), which in turn activates 6-phosphofructo-1-kinase (PFK-1) and glycolysis in the cytoplasm, however, in the nucleus F2,6BP activates Cdk1. Cdk1 is a central player in the cell cycle progression. F26BP stimulates Cdk-mediated phosphorylation of p27 at threonine 187, which in turn results in p27's uniquitination and proteasome degradation. A small molecule antagonist 3-(3-pyridinyl)-1-(4-pyridinyl)-2-propen-1-one (3PO) to FPKFB3 has been shown to increase unphosphorylated p27 protein[28].

Ovaries treated with 3PO generally contained fewer follicles than previously seen, additionally, several of the follicles seemed atretic. In spite of this poor foundation the healthy follicles were counted, and the result revealed that 3PO were able to promote primordial-to-primary transition. Previously, Sugiura (2004) implied that oocytes regulate glycolysis and the citric acid cycle in GCs, thereby providing nutritional support for the oocytes. Additionally, Boland (1994) ascertained that follicles predominately utilize glycolysis for energy production, and also follicular glycolysis is required for growth and estradiol secretion. This knowledge indicates that inhibition of glycolysis is an adverse, therefore another method must be used to investigate the effect of 3PO in the oocyte.

PRKAA1 The AMP-activated protein kinase (AMPK) is a sensor of cellular energy status and composed of a catalytic subunit a and two regulatory subunits: 13 and y. In mammalians, the catalytic subunit is encoded by two alternate genes: PRKAA1, PRKAA2. According to the transcriptomic data PRKAA1 is highly expressed in primordial follicles and IPA® analysis ascertained that it was involved with the mTOR pathway. AMPK is activated by metabolic stresses and xenobiotic compounds resulting in an imbalance of the cellular energy status caused by an increase in cellular ADP: ATP and/or AMP: ATP ratios. Once activated, AMPK switches on catabolic pathways generating ATP, while switching off biosynthetic pathways and cell-cycle progression, in the desire to restore the cellular energy homeostasis. Once AMPK is activated it will trigger acute effects on the metabolism, for instance, activated AMPK inhibits protein synthesis in two ways, first by phosphorylation of TSC2, second by directly phosphorylating Raptor, a subunit of the mTORC1 complex, both actions result in inactivation of mTORC1. Additionally, AMPK also activates glycolysis in monocytes and macrophages by phosphorylation and activation of the PFKFB3. This may allow macrophages to generate ATP efficiently in regions of infections or injury that are hypoxic. Since the transcriptomic data revealed that PFKFB3's expression was highly up regulated in primordial oocytes, this factor may be relevant. In addition to these acute effects on metabolism, AMPK also has effects on the transcription. AMPK directly phosphorylates Foxo3, activating transcription of many genes, including genes involved in resistance to oxidative stress and energy metabolism. Other effects of AMPK activation causes phosphorylation of p27 causing cell cycle arrest[31]. The results indicate that AICAR were able to suppress the primordial-to-primary follicle transition, since the ovaries treated with AICAR contained more primordial follicles as well as less primary and secondary follicles, most likely due to increased or decreased activation of Foxo3/p27 and mTORC1, respectively.

PDE

Cyclic nucleotide phosphodiesterases (PDEs) play critical roles in regulating intracellular cyclic nucleotides (Cyclic adenosine monophosphate (cAMP) and cyclic guanosine monophosphate (cGMP)) levels and compartmentalization via degradation of cyclic nucleotides[32,33]. Phosphodiesterase-3 (PDE3) is the major cAMP-hydrolyzing PDE present in VSMC and oocytes, and its inhibition by nitric oxide-induced accumulation of cGMP results in increased cAMP and protein kinase A (PKA) activity[32,34,35]. cAMP and cGMP are two very important second messengers involved in intracellular signal transduction in many cell types, including oocytes[36-38]. PDE3A-deficient oocytes exhibit cell cycle arrest at $G_2/M$ phase because increased cAMP/PKA signaling in KO oocytes most likely inhibits Cdc25B-catalyzed dephosphorylation/activation of Cdc2 (maturation promoting factor (MPF)), a key regulator of $G_2/M$ transition[24].

PDE3B

A role for PDE3B has not be reported. In our data, we find that antagonistic targeting of PDE3B resulted in activation of primordial follicles, suggesting Dyphylline as a potential target for the regulation of ovarian primordial follicles.

PDE8B

Guillemette et al. (2009) demonstrated that inhibition of PDE8 in cumulus cells increased cAMP in the cumulus-oocyte-complex, which resulted in delayed maturation of oocytes in bovine ovaries. Our results showed significantly more primordial follicles when ovaries were treated with the PDE8B inhibitor, suggesting ketotifen as a potential compounds towards primordial follicels conservation.

CPS1

The levels of ammonia appear to be elevated in women with reduced ovarian reserve and advanced maternal age (Pacella-ince et al. 2014). This indicates a decreased detoxification in these women. Because CPS1 is a part of the degradation of ammonia, it could have a beneficial effect to induce CPS1 in women with reduced ovarian reserve or advanced maternal age. Unfortunately, we were not able to get any statistical results from ovaries treated with a "protector" NCG of CPS1 because the dehydration protocol of the ovaries was not fully established. Nevertheless, oocytes seemed to be more naturally shaped than any of the other treatment forms. This might be due to an increase in survival. Therefore, further investigation on the effect of CPS1 will be needed to test our hypothesis.

CPS1 and Nrf2 were both found to be regulators of the intracellular environment and homeostasis. It would be fascinating to study the role of these molecules in women with reduced ovarian reserve and POI. In fact, investigations by Venkatesh et al. (2010) indicate that high levels of reactive oxygen species (ROS) are present in women with POI. Future research may want to investigate the level of ROS when using either a CPS1 "protector" or Nrf2 inhibitor.

Sequence List

```
PDGF-AA (peptide, expressed in E coli)
                                    SEQ ID NO: 1
MSIEEAVPAV CKTRTVIYEI PRSQVDPTSA NFLIWPPCVE

VKRCTGCCNT SSVKCQPSRV HHRSVKVAKV EYVRKKPKLK
```

-continued

EVQVRLEEHL ECACATSNLN PDHREEETGR RRESGKNRKR

KRLKPT

Items

The below items define preferred embodiments of the present disclosure

1. A compound for use in regulating follicle maturation, wherein said compound can regulate the activity of 6-phosphfructo-2-kinase.
2. The compound according to item 1, wherein said compound is an inhibitor of 6-phosphfructo-2-kinase.
3. The compound according to any of items 1 and 2, wherein said compound promotes follicle maturation.
4. The compound according to any of the preceding items, wherein said compound is 3-(3-pyridinyl)-1-(4-pyridinyl)-2-propen-1-one (3PO).
5. A compound for use in regulating follicle maturation, wherein said compound can regulate the activity of protein kinase AMP-activated catalytic subunit alpha 1 (PRKAA1).
6. The compound according to item 5, wherein said compound is an activator of PRKAA1.
7. The compound according to any of items 5 and 6, wherein said compound inhibits follicle maturation.
8. The compound according to any of items 5 to 7, wherein said compound is 5-aminoimidazole-4-carboxamide-1-β-D-ribofuranoside (AICAR).
9. A compound for use in regulating follicle maturation, wherein said compound can regulate the activity of Platelet-derived growth factor receptor—(PDGFRA)
10. The compound according to item 9, wherein said compound is an activator of PDGFRA.
11. The compound according to any of items 9 to 10, wherein said compound comprises an amino acid sequence having at least 80% sequence identity with SEQ ID NO: 1.
12. A compound for use in regulating follicle maturation, wherein said compound can regulate the activity of Phosphodiesterase 8B (PDE8B).
13. The compound according to item 12, wherein said compound is an inhibitor of PDE8B.
14. The compound according to any of items 12 to 13, wherein said compound inhibits follicle maturation.
15. The compound according to any of items 12 to 14, wherein said compound is 4,9-dihydro-4-(1-methyl-4-piperidylidende)-10H-benzo(4,5)cyclohepta(1,2,b)thiophen-10-one (Ketotifen).
16. A compound for use in regulating follicle maturation, wherein said compound can regulate the activity of Phosphodiesterase 3B (PDE3B).
17. The compound according to item 16, wherein said compound is an inhibitor of PDE3B.
18. The compound according to any of items 16 to 17, wherein said compound inhibits follicle maturation.
19. The compound according to any of items 16 to 18, wherein said compound is selected from the group consisting of 7-(2,3-dihydroxypropyl)-1,3-dimethylpurine-2,6-dione (dyphylline), 5-methyl-1H-1,6-naphthyridin-2-one (medorinone), 6-[4-(1-cyclohexyltetrazol-5-yl)butoxy]-3,4-dihydro-1H-quinolin-2-one (cilostazol), 2-[[2-[bis(2-hydroxyethyl)amino]-4,8-di(piperidin-1-yl)pyrimido[5,4-d]pyrimidin-6-yl]-(2-hydroxyethyl)amino]ethanol (dipyridamole), 3-amino-5-pyridin-4-yl-1H-pyridin-2-one (amrinone), 1-butyl-3-(4-methylphenyl)sulfonylurea (tolbutamide), 1,3-dimethyl-7H-purine-2,6-dione (theophylline) and 3,7-dimethyl-1-(5-oxohexyl)purine-2,6-dione (pentoxifylline).
20. A compound for use in regulating follicle maturation, wherein said compound can regulate the activity of Carbamoyl-Phosphate Synthase 1 (CPS1).
21. The compound according to item 20, wherein said compound is an inhibitor of CPS1.
22. The compound according to any of items 20 to 21, wherein said compound inhibits follicle maturation.
23. The compound according to any of items 20 to 22, wherein said compound is ((2S)-2-(carbamoylamino)pentanedioic acid (N-Carbamyl-L-glutamic acid).
24. A compound for use in regulating follicle maturation, wherein said compound can regulate the activity of Nuclear Factor, Erythroid 2 Like 2 (NFE2L2).
25. The compound according to item 24, wherein said compound is an inhibitor of NFE2L2.
26. The compound according to any of items 24 to 25, wherein said compound promotes follicle maturation.
27. The compound according to any of items 24 to 26, wherein said compound is 1-methylpyridin-1-ium-3-carboxylic acid; chloride (Trigonellin hydrochloride).
28. A compound for use in regulating follicle maturation, wherein said compound can regulate the activity of Protein Tyrosine Kinase 2 Beta (PTK2B).
29. The compound according to item 28, wherein said compound is an inhibitor of PTK2B.
30. The compound according to any of items 28 to 29, wherein said compound inhibits follicle maturation.
31. The compound according to any of items 28 to 30, wherein said compound is selected from the group consisting of N-methyl-N-[3-[[[2-[(2-oxo-1,3-dihydroindol-5-yl)amino]-5-(trifluoromethyl)pyrimidin-4-yl]amino]methyl]pyridin-2-yl]methanesulfonamide (PF-562271) and CT-707.
32. A compound for use in regulating follicle maturation, wherein said compound can regulate the activity of MDM2.
33. The compound according to item 32, wherein said compound is an inhibitor of MDM2.
34. The compound according to any of items 32 to 33, wherein said compound promotes follicle maturation.
35. The compound according to any of items 32 to 34, wherein said compound is selected from the group consisting of 1-N-[2-(1H-indol-3-yl)ethyl]-4-N-pyridin-4-ylbenzene-1,4-diamine (serdemetan), (1S)-1-(4-chlorophenyl)-6-methoxy-2-[4-[methyl-[[4-(4-methyl-3-oxopiperazin-1-yl)cyclohexyl]methyl]amino]phenyl]-7-propan-2-yloxy-1,4-dihydroisoquinolin-3-one (CGM097), L-Erythrohexonamide, 2,6-anhydro-5-((((3'R,4'S,5'R)-6"-chloro-4'-(2-chloro-3-fluoro-4-pyridinyl)-1",2"-dihydro-4,4-dimethyl-2"-oxodispiro(cyclohexane-1,2'-pyrrolidine-3',3"-(3H)indol)-5'-yl)carbonyl)amino)-3,4,5-trideoxy-, 4-methylbenzenesulfon (DS-3032b), 4-amino-1-[(2R,3S,4S,5R)-3,4-dihydroxy-5-(hydroxymethyl)oxolan-2-yl]pyrimidin-2-one (MK-8242), (6S)-5-(5-chloro-1,2-dihydro-1-methyl-2-oxo-3-pyridinyl)-6-(4-chlorophenyl)-2-(2,4-dimethoxy-5-pyrimidinyl)-5,6-dihydro-1-(1-methylethyl)-Pyrrolo[3,4-d]imidazol-4(1H)-one (HDM201), ALRN-6924, 4-{[(3S,4R,5S)-3-(3-Chloro-2-fluorophenyl)-4-(4-chloro-2-fluorophenyl)-4-cyano-5-(2,2-dimethylpropyl)-D-prolyl]amino}-3-methoxybenzoic acid (idasanutlin), RO6839921, [(4S,5R)-2-(4-tert-butyl-2-ethoxyphenyl)-4,5-bis(4-chlorophenyl)-4,5-dimethylimidazol-1-yl]-[4-(3-methylsulfonylpropyl)piperazin-1-yl]methanone (RO-5045337), 2-[(3R,5R,6S)-5-(3-chlorophenyl)-6-(4-chlorophenyl)-3-methyl-1-[(2S)-3-methyl-1-propan-2-ylsulfonylbutan-2-yl]-2-oxopiperidin-3-yl]acetic acid (AMG-232) and APG-115.

36. A compound for use in regulating follicle maturation, wherein said compound can regulate the activity of Erb-B2 Receptor Tyrosine Kinase 4 (ERBB4).

37. The compound according to item 36, wherein said compound is an inhibitor of Erb-B2 Receptor Tyrosine Kinase 4 (ERBB4).

38. The compound according to any of items 36 to 37, wherein said compound inhibits follicle maturation.

39. The compound according to any of items 36 to 38, wherein said compound is selected from the group consisting of [(3S)-morpholin-3-yl]methyl N-[4-[[1-[(3-fluorophenyl)methyl]indazol-5-yl]amino]-5-methylpyrrolo[2,1-f][1,2,4]triazin-6-yl]carbamate (BMS-599626), (E)-N-[4-(3-chloro-4-fluoroanilino)-7-[(3S)-oxolan-3-yl]oxyquinazolin-6-yl]-4-(dimethylamino)but-2-enamide (afatinib), N-[2-[2-(dimethylamino)ethyl-methylamino]-4-methoxy-5-[[4-(1-methylindol-3-yl)pyrimidin-2-yl]amino]phenyl]prop-2-enamide (osimertinib), 1-[4-[4-(3,4-dichloro-2-fluoroanilino)-7-methoxyquinazolin-6-yl]oxypiperidin-1-yl]prop-2-en-1-one (poziotinib), 4-methyl-N-[3-(4-methylimidazol-1-yl)-5-(trifluoromethyl)phenyl]-3-[(4-pyridin-3-ylpyrimidin-2-yl)amino]benzamide (pirotinib) and (E)-N-[4-(3-chloro-4-fluoroanilino)-3-cyano-7-ethoxyquinolin-6-yl]-4-(dimethylamino)but-2-enamide (pelitinib).

40. A compound for use in regulating follicle maturation, wherein said compound can regulate the activity of Dual Specificity Protein Kinase (TKK).

41. The compound according to item 40, wherein said compound is an inhibitor of TKK.

42. The compound according to any of items 40 to 41, wherein said compound inhibits follicle maturation.

43. The compound according to any of items 40 to 42, wherein said compound is methyl 2,6-dimethyl-5-nitro-4-[2-(trifluoromethyl)phenyl]-1,4-dihydropyridine-3-carboxylate (BAY 1217389).

44. A compound for use in regulating follicle maturation, wherein said compound can regulate the activity of B Lymphoid Tyrosine Kinase (BLK). 45. The compound according to item 44, wherein said compound is an inhibitor of BLK.

46. The compound according to any of items 44 to 45, wherein said compound inhibits follicle maturation.

47. The compound according to any of items 44 to 46, wherein said compound is N-[2-[2-(dimethylamino)ethyl-methylamino]-4-methoxy-5-[[4-(1-methylindol-3-yl)pyrimidin-2-yl]amino]phenyl]prop-2-enamide (osimertinib).

48. A compound for use in regulating follicle maturation, wherein said compound can regulate the activity of Insulin Like Growth Factor 1 Receptor (IGF1R).

49. The compound according to item 48, wherein said compound is an inhibitor of IGF1R.

50. The compound according to any of items 48 to 49, wherein said compound inhibits follicle maturation.

51. The compound according to any of items 48 to 50, wherein said compound is selected from the group consisting of (5R,5aR,8aS,9R)-5-hydroxy-9-(3,4,5-trimethoxyphenyl)-5a,6,8a,9-tetrahydro-5H-[2]benzofuro[5,6-f][1,3]benzodioxol-8-one (picropodophyllin), 3-[8-amino-1-(2-phenylquinolin-7-yl)imidazo[1,5-a]pyrazin-3-yl]-1-methylcyclobutan-1-ol)(LC Laboratories (linsitinib), cixutumumab, N-(2-chloro-6-methylphenyl)-2-[[6-[4-(2-hydroxyethyl)piperazin-1-yl]-2-methylpyrimidin-4-yl]amino]-1,3-thiazole-5-carboxamide (ganitumab), ((E)-N-[4-[3-chloro-4-(pyridin-2-ylmethoxy)anilino]-3-cyano-7-ethoxyquinolin-6-yl]-4-(dimethylamino)but-2-enamide (Neratinib), 4-N-(5-cyclopropyl-1H-pyrazol-3-yl)-6-(4-methylpiperazin-1-yl)-2-N-[(3-propan-2-yl-1,2-oxazol-5-yl)methyl]pyrimidine-2,4-diamine (XL228), 4-[4-[[4-chloro-3-(trifluoromethyl)phenyl]carbamoylamino]phenoxy]-N-methyl-pyridine-2-carboxamide (BIIB022), 4-amino-N-(1-azabicyclo[3.3.1]nonan-4-yl)-5-chloro-2-methoxybenzamide) (dalotuzumab) and MM-141.

52. A compound for use in regulating follicle maturation, wherein said compound can regulate the activity of Insulin Like Growth Factor 2 (IGF2).

53. The compound according to item 52, wherein said compound is an inhibitor of IGF2.

54. The compound according to any of items 52 to 53, wherein said compound inhibits follicle maturation.

55. The compound according to any of items 52 to 54, wherein said compound is BI 836845.

56. The compound according to any of the preceding items, for use in regulating follicle maturation in vitro.

57. The compound according to any of items 1 and 55, for use in regulating follicle maturation in vivo.

58. The compound according to any of the preceding items, wherein said compounds are for use in regulating primordial to primary transition of follicles.

59. The compound according to any of the preceding items, wherein said follicles are mammalian follicles.

60. The compound according to item 59, wherein said mammalian is a human.

61. A compound as defined in any of the preceding items for use in treating, preventing or ameliorating an ovulation disorder.

62. The compound according to item 61, wherein said ovulation disorder is selected from the group consisting of Polycystic ovary syndrome (PCOS), Premature ovarian failure (P01), Hypothalamic dysfunction and Menopause.

63. The compound according to item 61, wherein said ovulation disorder is caused by hyperprolactinemia.

64. A pharmaceutical composition comprising at least one compound according to any of items 1 to 57 for use in treating, preventing or ameliorating infertility or reduced fertility in a female individual.

65. The pharmaceutical composition according to item 64, further comprising at least one pharmaceutically acceptable carrier.

66. The pharmaceutical composition according to any of items 64 to 65, further comprising an additional active agent.

67. The pharmaceutical composition according to any of items 64 to 66, wherein said composition is administered in vitro to primordial follicles from said individual.

68. The pharmaceutical composition according to any of items 64 to 67, wherein said female individual is a female mammal.

69. The pharmaceutical composition according to any of item 68, wherein said female mammal is a female human.

70. A method for treating, preventing or ameliorating infertility of a female individual having an ovulation disorder, comprising administering to said individual a therapeutically effective amount of a compound as defined in any of items 1 to 57.

71. The method according to item 70, wherein said female individual is a female mammal, such as a female human.

72. A method for screening for a compound that regulates follicle maturation, wherein said method comprises a. selecting a compound known to regulate the activity of at least one of the candidates identified in table 1 and/or 2.

The invention claimed is:

1. A method for treating or ameliorating infertility or reduced fertility in a female individual, said method comprising administering to said individual a therapeutically effective amount of trigonelline or a pharmaceutically acceptable salt thereof.

2. The method of claim 1, wherein said trigonelline or pharmaceutically acceptable salt thereof promotes follicle maturation.

3. The method of claim 1, wherein said infertility or reduced fertility is influenced by an ovulation disorder.

4. The method of claim 3, wherein said ovulation disorder is selected from the group consisting of Polycystic ovary syndrome (PCOS), Premature ovarian failure (POI), Hypothalamic dysfunction, and Menopause.

5. The method of claim 1, wherein said trigonelline or pharmaceutically acceptable salt thereof is administered by a systemic administration route.

6. The method of claim 1, wherein said trigonelline or pharmaceutically acceptable salt thereof is administered to said individual by local administration to the ovaries.

7. The method of claim 1, wherein said method further comprises the steps of a. removing ovulated oocytes from said individual, after said administering said therapeutically effective amount of trigonelline or pharmaceutically acceptable salt thereof,
b. subjecting said ovulated oocyte to in vitro fertilization thereby obtaining a fertilized oocyte leading to a zygote,
c. culturing said zygote in order to obtain a multicellular blastocyst, and
d. transferring said multicellular blastocyst into the uterus of said individual and/or a surrogate mother.

8. The method of claim 1 wherein said individual is a human being.

9. The method of claim 1 wherein said pharmaceutically acceptable salt thereof comprises trigonelline and a pharmaceutically acceptable acid addition salt.

10. The method of claim 9 wherein said pharmaceutically acceptable acid addition salt is selected from the group consisting of: hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic.

* * * * *

SEQUENCE LISTING

<160> NUMBER OF SEQ ID NOS: 1

<210> SEQ ID NO 1
<211> LENGTH: 126
<212> TYPE: PRT
<213> ORGANISM: Homo sapiens

<400> SEQUENCE: 1

```
Met Ser Ile Glu Glu Ala Val Pro Ala Val Cys Lys Thr Arg Thr Val
1               5                   10                  15

Ile Tyr Glu Ile Pro Arg Ser Gln Val Asp Pro Thr Ser Ala Asn Phe
            20                  25                  30

Leu Ile Trp Pro Pro Cys Val Glu Val Lys Arg Cys Thr Gly Cys Cys
        35                  40                  45

Asn Thr Ser Ser Val Lys Cys Gln Pro Ser Arg Val His His Arg Ser
    50                  55                  60

Val Lys Val Ala Lys Val Glu Tyr Val Arg Lys Lys Pro Lys Leu Lys
65                  70                  75                  80

Glu Val Gln Val Arg Leu Glu Glu His Leu Glu Cys Ala Cys Ala Thr
                85                  90                  95

Ser Asn Leu Asn Pro Asp His Arg Glu Glu Glu Thr Gly Arg Arg Arg
            100                 105                 110

Glu Ser Gly Lys Asn Arg Lys Arg Lys Arg Leu Lys Pro Thr
        115                 120                 125
```